United States Patent
Dunn et al.

(10) Patent No.: US 7,348,345 B2
(45) Date of Patent: Mar. 25, 2008

(54) NONNUCLEOSIDE REVERSE TRANSCRIPTASE INHIBITORS

(75) Inventors: James Patrick Dunn, Los Altos, CA (US); Steven Swallow, Los Altos, CA (US); Zachary Kevin Sweeney, Redwood City, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/701,881

(22) Filed: Feb. 2, 2007

(65) Prior Publication Data

US 2007/0179157 A1 Aug. 2, 2007

Related U.S. Application Data

(62) Division of application No. 10/807,766, filed on Mar. 23, 2004, now Pat. No. 7,208,509.

(60) Provisional application No. 60/457,130, filed on Mar. 24, 2003.

(51) Int. Cl.
- *A61K 31/433* (2006.01)
- *A61K 31/4245* (2006.01)
- *A61K 31/4196* (2006.01)

(52) U.S. Cl. .............. 514/363; 514/364; 514/384

(58) Field of Classification Search ............... 514/363, 514/364, 384
See application file for complete search history.

(56) References Cited

U.S. PATENT DOCUMENTS

| | | |
|---|---|---|
| 3,274,185 A | 9/1966 | Sigal, Jr. et al. |
| 3,813,384 A | 5/1974 | Vogelsang et al. |
| 4,826,990 A | 5/1989 | Musser et al. |
| 4,942,236 A | 7/1990 | Musser et al. |
| 5,103,014 A | 4/1992 | Musser et al. |
| 6,248,769 B1 | 6/2001 | Cavalla et al. |

FOREIGN PATENT DOCUMENTS

| | | |
|---|---|---|
| EP | 0 273 309 B1 | 1/1995 |
| EP | 0 273 310 B1 | 6/1995 |
| WO | WO 97/40017 A2 | 10/1997 |
| WO | WO 02/36576 A1 | 5/2002 |

OTHER PUBLICATIONS

Graham, B.S., ("Clinical trials of HIV vaccines." HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM, pp. 1-20-38.*

Rosen, Gerald M., et al., "2-Benzyl-1,3,4-oxadiazolin-5-one and Related Compounds," *Notes*, Dept. of Chemistry, Clarkson College of Technology, Potsdam, NY, Aug. 1971, pp. 659-662.

De Clercq, Erik, "New Developments in Anti-HIV Chemotherapy," *Current Medicinal Chemistry*, 2001, pp. 1543-1572, vol. 8, No. 13, Bentham Science Publishers Ltd.

Buckheit, Jr., Robert W., Non-nucleoside reverse transcriptase inhibitors: perspectives on novel therapeutic compounds and strategies for the treatment of HIV infection, *Expert Opinion,.Investigative Drugs*, Ashley Publications, Ltd., 2001, pp. 1423-1442, vol. 10, No. 8.

Del Elmo, Esther, et al., "Anti-Trypanosoma Activity of Some Natural Stilbenoids and Synthetic Related Heterocyclic Compounds", *Bioorganic & Medicinal Chemistry Letters*, 2001, pp. 2755-2757, No. 11.

Del Elmo, Esther, et al., "Leishmanicidal Activity of Some Stilbenoids and Related Heterocyclic Compounds," *Bioorganic & Medicinal Chemistry Letters*, 2001, pp. 2123-2126, No. 11.

* cited by examiner

*Primary Examiner*—Rebecca Anderson
*Assistant Examiner*—Jason M Nolan
(74) *Attorney, Agent, or Firm*—Brian L. Buckwalter

(57) ABSTRACT

This invention relates to methods of treating an HIV infection with novel heterocyclic compounds of formula I wherein $R^1$–$R^4$, $X^1$ and $X^2$ are as defined in the summary and pharmaceutically acceptable salts, and methods to inhibit or modulate Human Immunodeficiency Virus (HIV) reverse transcriptase with compounds of formula I.

(I)

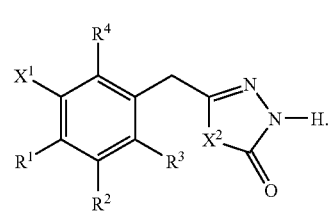

7 Claims, No Drawings

US 7,348,345 B2

NONNUCLEOSIDE REVERSE TRANSCRIPTASE INHIBITORS

CROSS REFERENCE TO PRIOR APPLICATION

This application is a divisional application of U.S. Ser. No. 10/807,766 filed Mar. 23, 2004 now U.S. Pat. 7,208,509 under Title 35 U.S.C. 121, which claims benefit of U.S. Provisional Application No. 60/457,130, filed Mar. 24, 2003, which is hereby incorporated by reference in its entirety. The related application, now U.S. Ser. No. 10/807,993, filed Mar. 23, 2004 entitled Non-Nucleoside Reverse Transcriptase Inhibitors (J. P. Dunn et al.), is hereby incorporated by reference in its entirety.

FIELD OF THE INVENTION

The invention relates to the field of antiviral therapy and, in particular, to non-nucleoside reverse transcriptase inhibitors for treating Human Immunodeficiency Virus (HIV) mediated diseases. The invention provides novel heterocyclic compounds, pharmaceutical compositions comprising these compounds, methods for treatment or prophylaxis of HIV mediated diseases employing said compounds in monotherapy or in combination therapy, and a process for preparing novel heterocyclic compounds.

BACKGROUND OF THE INVENTION

The human immunodeficiency virus HIV is the causative agent of acquired immunodeficiency syndrome (AIDS), a disease characterized by the destruction of the immune system, particularly of the $CD4^+$ T-cell, with attendant susceptibility to opportunistic infections. HIV infection is also associated with a precursor AIDS—related complex (ARC), a syndrome characterized by symptoms such as persistent generalized lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Currently available chemotherapy targets two crucial viral enzymes: HIV protease and HW reverse transcriptase. (J. S. G. Montaner et al. Antiretroviral therapy: "the state of the art", Biomed & Pharmacother. 1999 53:63-72; R. W. Shafer and D. A. Vuitton, *Highly active retroviral therapy (HAART) for the treatment of infection with human immunodeficiency virus type 1*, Biomed. & Pharmacother. 1999 53:73-86; E. De Clercq, *New Developments in Anti-HIV Chemotherapy*. Curr. Med. Chem. 2001 8:1543-1572). Two general classes of RTI inhibitors have been identified: nucleoside reverse transcriptase inhibitors (NRTI) and non-nucleoside reverse transcriptase inhibitors (NNRTI).

NRTIs typically are 2',3'-dideoxynucleoside (ddN) analogs which must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation. Currently clinically used NRTIs include zidovudine (AZT), didanosine (ddI), zalcitabine (ddC), stavudine (d4T), lamivudine (3TC) and tenofovir (PMPA).

NNRTIs were first discovered in 1989. NNRTI are allosteric inhibitors which bind reversibly at a nonsubstrate binding site on the HIV reverse transcriptase thereby altering the shape of the active site or blocking polymerase activity. (R. W. Buckheit, Jr., *Non-nucleoside reverse transcriptase inhibitors: perspectives for novel therapeutic compounds and strategies for treatment of HIV infection*, Expert Opin. Investig. Drugs 2001 10(8)1423-1442; E. De Clercq *The role of non0-nuceloside reverse transcriptase inhibitors (NNRTIs) in the therapy of HIV-1 infection*, Antiviral Res. 1998 38:153-179; G. Moyle, *The Emerging Roles of Non-Nucleoside Reverse Transcriptase Inhibitors in Antiviral Therapy*, Drugs 2001 61(1):19-26) Although over thirty structural classes of NNRTIs have been identified in the laboratory, only three compounds have been approved for HIV therapy: efavirenz, nevirapine and delavirdine. Although initially viewed as a promising class of compounds, in vitro and in vivo studies quickly revealed the NNRTIs presented a low barrier to the emergence of drug resistant HIV strains and class-specific toxicity. Drug resistance frequently develops with only a single point mutation in the RT.

While combination therapy with NRTIs, PIs and NNRTIs has, in many cases, dramatically lowered viral loads and slowed disease progression, significant therapeutic problems remain. The cocktails are not effective in all patients, potentially severe adverse reactions often occur and the rapidly-replicating HIV virus has proven adroit at creating mutant drug-resistant variants of wild type protease and reverse transcriptase.

There remains a need for safer drugs with activity against wild type and commonly occurring resistant strains of HIV. Benzyl-pyridazinone compounds have been extensively investigated as thyroxin analogs which can decrease plasma cholesterol without stimulating cardiac activity (A. H. Underwood et al. *A thyromimetic that decreases plasma cholesterol without increasing cardiovascular activity* Nature 1986 324(6096):425429; P. D. Leeson et al. *Selective thyromimetics. Cardiac-sparing thyroid hormone analogs containing 3'-arylmethyl substituents* J. Med Chem 1989 32(2):320-326; P. D. Leeson et al. EP 0188351). WO9624343 (D. J. Dunnington) discloses oxo-pyridazinyl-methyl substituted tyrosines are selective antagonists for the haematopoietic phosphatase SH2 domain which may render them useful to increase erythropoiesis and haematopoiesis. WO 9702023 (D. J. Dunnington) and WO9702024 (D. J. Dunnington) further disclose these compounds are specific inhibitors of the human Stat 6 SH2 domain and may be useful for treating asthma, allergic rhinitis and anemia. WO2001085670 (H. Shiohara et al.) discloses related malonamide derivatives useful for treating circulatory diseases. EP 810218 (D. A. Allen et al.) discloses benzoyl substituted benzyl-pyridazinone compounds which are cyclooxygenase inhibitors and potential antiinflammatory or analgesic compounds. None of the references teaches therapy for HIV infections or inhibition of HIV reverse transcriptase.

SUMMARY OF THE INVENTION

The present invention relates to a compounds according to formula I, methods for treating diseases mediated by human immunodeficiency virus by administration of a compound according to formula I, pharmaceutical compositions for treating diseases mediated by human immunodeficiency virus containing a compound according to formula I, and processes to prepare a compound according to formula I

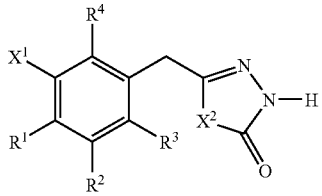

(I)

wherein;

$X^1$ is selected from the group consisting of $R^5O$, $R^5S(O)_n$, $R^5CH_2$, $R^5CH_2O$, $R^5CH_2S(O)_n$, $R^5OCH_2$, $R^5S(O)_nCH_2$ and $NR^5R^6$;

$X^2$ is selected from the group consisting of o-phenylene, 1,2-cyclohexenylene, O, S, and $NR^7$;

$R^1$ and $R^2$ are (i) each independently selected from the group consisting of hydrogen, $C_{1-6}$ alkyl, $C_{1-6}$ haloalkyl, $C_{3-8}$ cycloalkyl, $C_{1-6}$ alkylthio, $C_{1-6}$ alkylsulfinyl, $C_{1-6}$ alkylalkylsulfonyl, $C_{1-6}$ haloalkoxy, $C_{1-6}$ haloalkylthio, halogen, amino, alkylamino, dialkylamino, aminoacyl, nitro and cyano; or, (ii) taken together are —CH=CH—CH=CH—; or, (iii) taken together along with the carbons to which they are attached to form a five- or six-membered heteroaromatic or heterocyclic ring with a one or two heteroatoms independently selected from the group consisting of O, S and NH;

$R^3$ and $R^4$ are each independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ haloalkoxy, $C_{1-6}$ haloalkylthio, halogen, amino, alkylamino, dialkylamino, aminoacyl, nitro and cyano;

$R^5$ is selected from the group consisting of phenyl, naphthyl, pyridinyl, pyridinyl N-oxide, indolyl, indolyl N-oxide, quinolinyl, quinolinyl N-oxide, pyrimidinyl, pyrazinyl and pyrrolyl; wherein, said phenyl, said naphthyl, said pyridinyl, said pyridinyl N-oxide, said indolyl, said indolyl N-oxide, said quinolinyl, said quinolinyl N-oxide, said pyrimidinyl, said pyrazinyl and said pyrrolyl groups are optionally substituted with one to three substituents independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ alkylalkylsulfonyl, $C_{1-6}$ haloalkoxy, $C_{1-6}$ haloalkylthio, halogen, amino, alkylamino, dialkylamino, aminoacyl, acyl, alkoxycarbonyl, carbamoyl, N-alkylcarbamoyl, N,N-dialkylcarbamoyl, nitro and cyano;

$R^6$ is hydrogen, $C_{1-6}$ alkyl, or acyl;

$R^7$ is hydrogen or $C_{1-6}$ alkyl optionally substituted with one or two substituents independently selected from the group consisting of hydroxy, alkoxy, thiol, alkylthio, $C_{1-6}$ alkylsulfinyl, $C_{1-6}$ alkylsulfonyl, halogen, amino, alkylamino, dialkylamino, aminoalkyl, alkylaminoalkyl, and dialkylaminoalkyl;

n is an integer from 0 to 2; and, hydrates, solvates, clathrates and acid addition salts thereof, with the proviso that if $X^2$ is ortho-phenylene, $R^5$ can not unsubstituted phenyl.

The invention also relates to a process for preparing a compound according to formula I wherein $X^1$ is $OR^5$ or $SR^5$, $R^5$ is an optionally substituted aryl and $R^1$—$R^4$, $R^7$ and $X^2$ are as defined hereinabove

DETAILED DESCRIPTION OF THE INVENTION

In one embodiment of the invention there is provided a compound according to formula I,

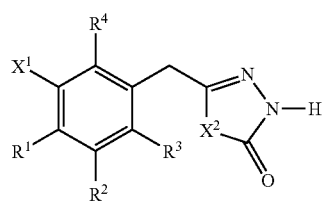

(I)

wherein $X^1$, $X^2$, $R^1$, $R^2$, $R^3$, $R^4$, $R^5$, $R^6$, and $R^7$ are as defined hereinabove, and hydrates, solvates, clathrates and acid addition salts thereof.

In another embodiment of the invention there is provided a compound according to formula I wherein $X^1$ is $OR^5$ or $SR^5$; $R^3$ is hydrogen or fluoro; $R^4$ is selected from the group consisting of hydrogen, chloro, fluoro and methyl; $R^5$ is optionally substituted phenyl; and, $R^1$, $R^2$, $R^7$, $X^2$ and n are as defined hereinabove.

In another embodiment of the present invention there is provided a compound according to formula I wherein $X^1$ is $OR^5$ or $SR^5$; $R^1$ is methyl, ethyl, trifluoromethyl or halogen; $R^3$ is hydrogen or fluoro; $R^4$ is selected from the group consisting of hydrogen, chloro, fluoro and methyl; $R^5$ is optionally substituted phenyl; and, $R^2$, $R^7$, $X^2$ and n are as defined hereinabove.

In another embodiment of the present invention there is provided a compound according to formula I wherein $X^1$ is $OR^5$ or $SR^5$; $R^1$ is methyl, ethyl, trifluoromethyl or halogen; $R^3$ is hydrogen or fluoro; $R^4$ is selected from the group consisting of hydrogen, chloro, fluoro and methyl; $R^5$ is monosubstituted phenyl; and, $R^2$, $R^7$, $X^2$ and n are as defined hereinabove.

In another embodiment of the present invention there is provided a compound according to formula I wherein $X^1$ is $OR^5$ or $SR^5$; $R^1$ is methyl, ethyl, trifluoromethyl or halogen; $R^3$ is hydrogen or fluoro; $R^4$ is selected from the group consisting of hydrogen, chloro, fluoro and methyl; $R^5$ is 2,5-disubstituted phenyl; and, $R^2$, $R^7$, $X^2$ and n are as defined hereinabove.

In another embodiment of the present invention there is provided a compound according to formula I wherein $X^1$ is $OR^5$ or $SR^5$; $R^1$ is methyl, ethyl, trifluoromethyl or halogen; $R^3$ is hydrogen or fluoro; $R^4$ is selected from the group consisting of hydrogen, chloro, fluoro and methyl; $R^5$ is 3,5-disubstituted phenyl; and, $R^2$, $R^7$, $X^2$ and n are as defined hereinabove.

In another embodiment of the present invention there is provided a compound according to formula I wherein $X^1$ is $OR^5$ or $SR^5$; $R^1$ is methyl, ethyl, trifluoromethyl or halogen; $R^3$ is hydrogen or fluoro; $R^4$ is selected from the group consisting of hydrogen, chloro, fluoro and methyl, $R^5$ is 2,4-disubstituted phenyl; and $R^2$, $R^7$, $X^2$ and n are as defined hereinabove.

In another embodiment of the present invention there is provided a compound according to formula I wherein $X^1$ is $OR^5$ or $SR^5$; $R^1$ is methyl, ethyl, trifluoromethyl or halogen; $R^3$ is hydrogen or fluoro; $R^4$ is selected from the group consisting of hydrogen, chloro, fluoro and methyl; $R^5$ is 2,6-disubstituted phenyl; and, $R^2$, $R^7$, $X^2$ and n are as defined hereinabove.

In another embodiment of the present invention there is provided a compound according to formula I wherein $X^1$ is $OR^5$ or $SR^5$; $R^1$ and $R^2$ are independently hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkoxy, $C_{1-6}$ haloalkylthio, halogen, amino, alkylamino, dialkylamino, aminoacyl, nitro and cyano; $R^3$ is hydrogen or fluoro; and, $R^4$, $R^5$, $R^7$, $X^2$ and n are as defined hereinabove.

In another embodiment of the present invention there is provided a compound according to formula I wherein $X^1$ is $OR^5$; $R^1$ is methyl, ethyl, trifluoromethyl or halogen; $R^2$ and $R^4$ are independently hydrogen, fluoro, chloro, methyl or ethyl; $R^3$ is hydrogen or fluoro; $R^5$ is optionally substituted phenyl; n is 0 to 2; and $R^7$ and $X^2$ are as defined hereinabove.

In another embodiment of the present invention there is provided a compound according to formula I wherein $X^1$ is $OR^5$; $R^1$ is methyl, ethyl, trifluoromethyl or halogen; $R^2$ and $R^4$ are independently hydrogen, fluoro, chloro, methyl or ethyl; $R^3$ is hydrogen or fluoro; $R^5$ is monosubstituted phenyl; n is 0 to 2; and $R^7$ and $X^2$ are as defined hereinabove.

In another embodiment of the present invention there is provided a compound according to formula I wherein $X^1$ is $OR^5$; $R^1$ is methyl, ethyl, trifluoromethyl or halogen; $R^2$ and $R^4$ are independently hydrogen, fluoro, chloro, methyl or ethyl; $R^3$ is hydrogen or fluoro; $R^5$ is monosubstituted phenyl and the substituent is selected from the group consisting of halogen, cyano, $Cl_4$ alkyl, $C_{1-6}$ haloalkyl, $C_{1-6}$ alkoxy, $C_{1-6}$ alkylthio and $C_{1-6}$ haloalkoxy; and, $R^4$, $R^7$, $X^2$ and n are as defined hereinabove.

In another embodiment of the present invention there is provided a compound according to formula I wherein $X^1$ is $OR^5$; $R^1$ is methyl, ethyl, trifluoromethyl or halogen; $R^2$ and $R^4$ are independently hydrogen, fluoro, chloro, methyl or ethyl; $R^3$ is hydrogen or fluoro; $R^5$ is 2,5-disubstituted phenyl; n is 0 to 2; and $R^7$ and $X^2$ are as defined hereinabove.

In another embodiment of the present invention there is provided a compound according to formula I wherein $X^1$ is $OR^5$; $R^1$ is methyl, ethyl, trifluoromethyl or halogen; $R^2$ and $R^4$ are independently hydrogen, fluoro, chloro, methyl or ethyl; $R^3$ is hydrogen or fluoro; $R^5$ is 2,5-disubstituted phenyl and the substituents are independently selected from the group consisting of halogen, cyano, $C_{1-6}$ alkyl, $C_{1-6}$ haloalkyl, $C_{1-6}$ alkoxy, $C_{1-6}$ alkylthio and $C_{1-6}$ haloalkoxy; and, $R^4$, $R^7$, $X^2$ and n are as defined hereinabove.

In another embodiment of the present invention there is provided a compound according to formula I wherein $X^1$ is $OR^5$; $R^1$ is methyl, ethyl, trifluoromethyl or halogen; $R^2$ and $R^4$ are independently hydrogen, fluoro, chloro, methyl or ethyl; $R^3$ is hydrogen or fluoro; $R^5$ is 3,5-disubstituted phenyl; n is 0 to 2; and $R^7$ and $X^2$ are as defined hereinabove.

In another embodiment of the present invention there is provided a compound according to formula I wherein $X^1$ is $OR^5$; $R^1$ is methyl, ethyl, trifluoromethyl or halogen; $R^2$ and $R^4$ are independently hydrogen, fluoro, chloro, methyl or ethyl; $R^3$ is hydrogen or fluoro; $R^5$ is 3,5-disubstituted phenyl and the substituents are independently selected from the group consisting of halogen, cyano, $C_{1-6}$ alkyl, $C_{1-6}$ haloalkyl, $C_{1-6}$ alkoxy, $C_{1-6}$ alkylthio and $C_{1-6}$ haloalkoxy; and, $R^4$, $R^7$, $X^2$ and n are as defined hereinabove.

In another embodiment of the present invention there is provided a compound according to formula I wherein $X^1$ is $OR^5$; $R^1$ is methyl, ethyl, trifluoromethyl or halogen; $R^2$ and $R^4$ are independently hydrogen, fluoro, chloro, methyl or ethyl; $R^3$ is hydrogen or fluoro; $R^5$ is 2,4-disubstituted phenyl; n is 0 to 2; and $R^7$ and $X^2$ are as defined hereinabove.

In another embodiment of the present invention there is provided a compound according to formula I wherein $X^1$ is $OR^5$; $R^1$ is methyl, ethyl, trifluoromethyl or halogen; $R^2$ and $R^4$ are independently hydrogen, fluoro, chloro, methyl or ethyl; $R^3$ is hydrogen or fluoro; $R^5$ is 2,4-disubstituted phenyl and the substituents are independently selected from the group consisting of halogen, cyano, $C_{1-6}$ alkyl, $C_{1-6}$ haloalkyl, $C_{1-6}$ alkoxy, $C_{1-6}$ alkylthio and $C_{1-6}$ haloalkoxy; and, $R^4$, $R^7$, $X^2$ and n are as defined hereinabove.

In another embodiment of the present invention there is provided a compound according to formula I wherein $X^1$ is $OR^5$; $R^1$ is methyl, ethyl, trifluoromethyl or halogen; $R^2$ and $R^4$ are independently hydrogen, fluoro, chloro, methyl or ethyl; $R^3$ is hydrogen or fluoro; $R^5$ is 2,6-disubstituted phenyl; n is 0 to 2; and $R^7$ and $X^2$ are as defined hereinabove.

In another embodiment of the present invention there is provided a compound according to formula I wherein $X^1$ is $OR^5$; $R^1$ is methyl, ethyl, trifluoromethyl or halogen; $R^2$ and $R^4$ are independently hydrogen, fluoro, chloro, methyl or ethyl; $R^3$ is hydrogen or fluoro; $R^5$ is 2,6-disubstituted phenyl and the substituents are independently selected from the group consisting of halogen, cyano, $C_{1-6}$ alkyl, $C_{1-6}$ haloalkyl, $C_{1-6}$ alkoxy, $C_{1-6}$ alkylthio and $C_{1-6}$ haloalkoxy; and, $R^4$, $R^7$, $X^2$ and n are as defined hereinabove.

In another embodiment of the present invention there is provided a compound according to formula I wherein $X^1$ is $OR^5$ or $SR^5$; $R^3$ and $R^4$ are independently hydrogen, chloro, fluoro or methyl; $R^5$ is optionally substituted pyridinyl, pyridinyl N-oxide, indolyl, indolyl N-oxide, quinolinyl, quinolinyl N-oxide, pyrimidinyl, pyrazinyl and pyrrolyl; and, $X^2$, $R^1$, $R^2$, $R^3$, $R^7$ and n are as defined hereinabove.

In another embodiment of the present invention there is provided a compound according to formula I wherein $R^1$ and $R^2$ along with the carbon atoms to which they are attached form a phenyl, dihydropyran, dihydrofuran or furan ring; and, $X^1$, $X^2$, $R^3$, $R^4$, $R^5$, $R^6$, $R^7$ and n are as defined hereinabove.

In another embodiment of the present invention there is provided a compound according to formula I wherein $X^1$ is $OR^5$ or $SR^5$; $R^1$ and $R^2$ along with the carbon atoms to which they are attached form a phenyl, dihydropyran, dihydrofuran or furan ring; $R^3$ is hydrogen, $R^4$ is hydrogen or fluoro; $R^5$ is optionally substituted phenyl; and, $X^2$, $R^7$ and n are as defined hereinabove.

In another embodiment of the present invention there is provided a method for treating an HIV infection, or preventing an HIV infection, or treating AIDS or ARC, comprising administering to a host in need thereof a therapeutically effective amount of a compound of formula I

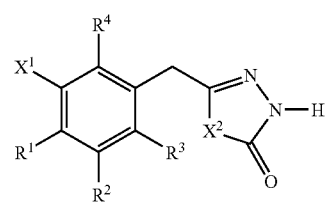

(I)

wherein, $X^1$, $X^2$, $R^1$, $R^2$, $R^3$, $R^4$, $R^5$, $R^6$, $R^7$ and n are as defined hereinabove, and hydrates, solvates, clathrates and acid addition salts thereof.

In another embodiment of the present invention there is provided a method for treating an HIV infection, or preventing an HIV infection, or treating AIDS or ARC, comprising administering to a host in need thereof a therapeutically effective amount of a compound of formula I wherein: $X^1$ is $OR^5$; $R^1$ is methyl, ethyl, trifluoromethyl or halogen; $R^2$ and $R^4$ are independently hydrogen, fluoro, chloro, methyl or ethyl;

$R^3$ is hydrogen or fluoro; $R^5$ is optionally substituted phenyl; and, $X^2$, $R^7$ and n are as defined hereinabove.

In another embodiment of the present invention there is provided a method for treating an HIV infection, or preventing an HIV infection, or treating AIDS or ARC, comprising co-administering to a host in need thereof a therapeutically effective amount of a compound of formula I wherein, $X^1$, $X^2$, $R^1$, $R^2$, $R^3$, $R^4$, $R^5$, $R^6$, $R^7$ and n are as defined hereinabove, and hydrates, solvates, clathrates and acid addition salts thereof, and at least one compound selected from the group consisting of HIV protease inhibitors, nucleoside reverse transcriptase inhibitors, non-nucleoside reverse transcriptase inhibitors, CCR5 inhibitors and viral fusion inhibitors.

In another embodiment of the present invention there is provided a method for treating an HIV infection, or preventing an HIV infection, or treating AIDS or ARC, comprising co-administering to a host in need thereof a therapeutically effective amount of a compound of formula I wherein, $X^1$, $X^2$, $R^1$, $R^2$, $R^3$, $R^4$, $R^5$, $R^6$, $R^7$ and n are as defined hereinabove, and hydrates, solvates, clathrates and acid addition salts thereof, and at least one compound selected from the group consisting of zidovudine, lamivudine, didanosine, zalcitabine, stavudine, rescriptor, sustiva, viramune efavirenz, nevirapine and delavirdine and/or the group consisting of saquinavir, ritonavir, nelfinavir, indinavir, amprenavir and lopinavir.

In another embodiment of the present invention there is provided a method for inhibiting a retrovirus reverse transcriptase comprising administering a compound of formula I wherein, $X^1$, $X^2$, $R^1$, $R^2$, $R^3$, $R^4$, $R^5$, $R^6$, $R^7$ and n are as defined hereinabove, and hydrates, solvates, clathrates and acid addition salts thereof.

In another embodiment of the present invention there is provided a method for inhibiting a retrovirus reverse transcriptase having at least one mutation with respect to wild type virus comprising administering to a host in need thereof, a therapeutically effective amount of a compound of formula I wherein, $X^1$, $X^2$, $R^1$, $R^2$, $R^3$, $R^4$, $R^5$, $R^6$, $R^7$ and n are as defined hereinabove; and, hydrates, solvates, clathrates; and, acid addition salts thereof.

In another embodiment of the present invention there is provided a method treating an HIV infection, or preventing an HIV infection, or treating AIDS or ARC, wherein the host is infected with a strain of HIV which exhibits reduced susceptibility to efavirenz, nevirapine or delavirdine comprising administering to a host in need thereof a therapeutically effective amount of a compound of formula I wherein, $X^1$, $X^2$, $R^1$, $R^2$, $R^3$, $R^4$, $R^5$, $R^6$, $R^7$ and n are as defined hereinabove; and, hydrates, solvates, clathrates and acid addition salts thereof.

In another embodiment of the present invention there is provided a pharmaceutical composition comprising a therapeutically effective quantity of a compound of formula I wherein, wherein, $X^1$, $X^2$, $R^1$, $R^2$, $R^3$, $R^4$, $R^5$, $R^6$, $R^7$ and n are as defined hereinabove, and hydrates, solvates, clathrates and acid addition salts thereof with the proviso that if $X^2$ is ortho-phenylene, $R^5$ can not unsubstituted phenyl, in admixture with at least one pharmaceutically acceptable carrier or diluent sufficient upon administration in a single or multiple dose regimen for treating diseases mediated by human immunodeficiency virus inhibit HIV.

In another embodiment of the present invention there is provided a process for preparing a heterocycle of formula I, wherein $X^1$ is $OR^5$ or $OCH_2R^5$ and $R^5$ is an optionally substituted aryl, or heteroaryl moiety; $X^2$ is O, S, or $NR^7$ and $R^1$-$R^4$ and $R^7$ are as defined hereinabove,

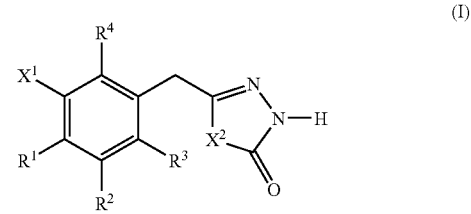

which process comprises the steps of: (i)(a) coupling an aryl compound of formula IIa wherein $X^4$ is hydrogen, alkoxycarbonyl or CN, with (A) an arylboronic acid or an aryl halide, or (B) an aralkyl halide to produce an ether of formula IIb; and, if $X^4$ is hydrogen;

(b) (A) brominating the methyl group with N-bromosuccinimide and (B) displacing the bromide ($X^4$=Br) with sodium cyanide to produce the corresponding nitrile ($X^4$=CN), and, optionally, (C) hydrolyzing the nitrile to an alkoxycarbonyl ($X^4$=$CO_2$alkyl) or an O-alkyl imidate hydrochloride ($X^4$=C(=$NH_2^+$) OR $Cl^-$);

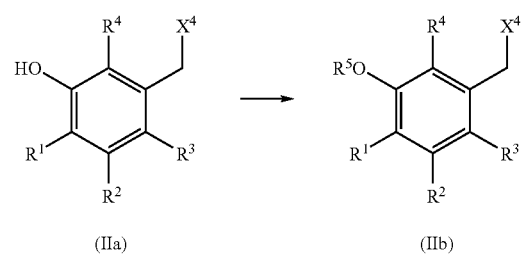

(ii)(A) treating a compound of formula IIb ($X^4$=alkoxycarbonyl) sequentially with hydrazine hydrate to form the acyl hydrazide (IIb; $X^4$=CONHNH$_2$) and, (a) phosgene, or a phosgene equivalent, to produce an oxadiazolone of formula I wherein $X^2$ is O; or, (b) sequentially with an alkyl isocyanate ($R^7$NCO) to produce a diacylhydrazone (IIb; $X^4$=C(=O)NHNHC(=O)NHR$^7$) and with base to produce the triazolone I ($X^2$=NR$^7$); or, (B) treating a nitrile of formula IIb ($X^4$=CN) sequentially (a) with acid and alcohol to produce the O-alkyl imidate hydrochloride ($X^4$=C(=$NH_2^+$)OR $Cl^-$), (b) with O-methylthiocarbazine (NH$_2$NHC(=S)OMe)to produce IIb wherein

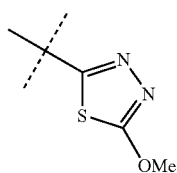

(III)

$X^4$ is a methoxythiadiazoline according to formula (III), and (c) with aqueous acid to hydrolyze said methoxythiadiazoline and produce a compound of formula I wherein $X^2$ is S.

In another embodiment of the present invention there is provided a process as described above for preparing a compound of formula I wherein $X^1$ is $OR^5$, $R^5$ is optionally substituted aryl or heteroaryl and the ether is prepared by coupling an arylboronic acid and a phenol IIa in the presence of a Cu(II) salt.

In another embodiment of the present invention there is provided a process as described above for preparing a compound of formula I wherein $X^1$ is $OR^5$, $R^5$ is optionally substituted aryl or heteroaryl and the ether is prepared by coupling an aryl halide and a phenol IIa in the presence of a Cu(I) salt.

In another embodiment of the present invention there is provided a process as described above for preparing a compound of formula I wherein $X^1$ is $OCH_2R^5$ or $OR^5$, $R^5$ is an optionally substituted aryl or heteroaryl moiety and the ether is prepared by coupling an aryl halide or heteroaryl halide further substituted by electron withdrawing groups, or an optionally substituted aralkyl halide and a phenol IIa, in the presence of a base.

In another embodiment of the present invention there is provided a process as described above for preparing a compound of formula I wherein $X^1$ is —$OCH_2R^5$, $R^5$ is optionally substituted aryl and the ether is formed by coupling an alcohol $R^5CH_2OH$ and IIa said coupling catalyzed by an a dialkylazodicarboxylate and triaryl or trialkylphosphine.

In another embodiment of the present invention there is provided a process as described above for preparing an oxadiazolone compound of formula I by treating a compound of formula IIb wherein $X^1$ is $OR^5$ or —$OCH_2R^5$, $R^5$ is optionally substituted aryl or heteroaryl, $X^4$ is C(=O)NHNH$_2$ with phosgene.

In another embodiment of the present invention there is provided a process as described above for preparing an oxadiazolone compound of formula I by treating a compound of formula IIb wherein $X^1$ is $OR^5$ or —$OCH_2R^5$, $R^5$ is optionally substituted aryl or heteroaryl, $X^4$ is C(=O)NHNH$_2$ with carbonyl diimidazole.

In another embodiment of the present invention there is provided a process as described above for preparing a triazolone compound of formula I by treating a compound of formula IIb wherein $X^1$ is $OR^5$ or —$OCH_2R^5$, $R^5$ is optionally substituted aryl, $X^4$ is C(=O)NHNH$_2$ sequentially with methyl isocyanate or ethyl isocyanate and methanolic sodium hydroxide.

In another embodiment of the present invention there is provided a process as described above for preparing a thiadiazolone compound of formula I by treating a compound of formula IIb wherein $X^1$ is $OR^5$ or —$OCH_2R^5$, $R^5$ is optionally substituted aryl, $X^4$ is C(=NH$_2^+$) Cl$^-$ sequentially with hydrazinecarbothioic acid O-methyl ester and aqueous acid.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition provided in the Summary of the Invention.

The term "$C_{1-6}$ alkyl" as used herein denotes an unbranched or branched chain, saturated, monovalent hydrocarbon residue containing 1 to 6 carbon atoms. Examples of alkyl groups include, but are not limited to, lower alkyl groups include methyl, ethyl, propyl, i-propyl, n-butyl, i-butyl, t-butyl or pentyl, isopentyl, neopentyl, hexyl.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl.

The term "aryl" as used herein means a monocyclic or polycyclic-aromatic group comprising carbon and hydrogen atoms. Examples of suitable aryl groups include, but are not limited to, phenyl, tolyl, indenyl, and 1- or 2-naphthyl, as well as benzo-fused carbocyclic moieties such as 5,6,7,8-tetrahydronaphthyl. An aryl group can be unsubstituted or substituted with one or more suitable substituents which substituents include $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkoxy, $C_{1-6}$ haloalkylthio, halogen, amino, alkylamino, dialkylamino, aminoacyl, acyl, alkoxycarbonyl, carbamoyl, N-alkylcarbamoyl, N,N-dialkylcarbamoyl, nitro and cyano.

A "heteroaryl group" or "heteroaromatic" as used herein means a monocyclic- or polycyclic aromatic ring comprising 15 carbon atoms, hydrogen atoms, and one or more heteroatoms, preferably, 1 to 3 heteroatoms, independently selected from nitrogen, oxygen, and sulfur. As well known to those skilled in the art, heteroaryl rings have less aromatic character than their all-carbon counter parts. Thus, for the purposes of the invention, a heteroaryl group need only have some degree of aromatic character. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, thienyl, isoxazolyl, indolyl, quinolinyl, and oxazolyl. A heteroaryl group can be unsubstituted or substituted with one or more suitable substituents selected from hydroxy, oxo, cyano, alkyl, alkoxy, haloalkoxy, alkylthio, halo, haloalkyl, nitro, alkoxycarbonyl, amino, alkylamino, dialkylamino, aminoacyl, alkylsulfonyl, arylsulfmyl, alkoxycarbonyl, carbamoyl, N-alkylcarbamoyl, N,N-dialkylcarbamoyl, acyl unless otherwise indicated. A nitrogen atom in the heteroaryl ring can optionally be an N-oxide.

The term "heterocyclyl" means the monovalent saturated cyclic radical, consisting of one or more rings, preferably one to two rings, of three to eight atoms per ring, incorporating one or more ring heteroatoms (chosen from N,O or $S(O)_{0-2}$), and which can optionally be substituted with one or more, preferably one to three substituents selected from hydroxy, oxo, cyano, alkyl, alkoxy, haloalkoxy, alkylthio, halo, haloalkyl, nitro, alkoxycarbonyl, amino, alkylamino, dialkylamino, aminoacyl, alkylsulfonyl, arylsulfinyl, alkoxycarbonyl, carbamoyl, N-alkylcarbarnoyl, N,N-dialkylcarbamoyl, acyl unless otherwise indicated. Examples of heterocyclic radicals include, but are not limited to, firanyl, tetrahydropyranyl, tetrahydrothiophenyl and the like.

The term "alkoxy group" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, heptyloxy including their isomers.

The term "alkylthio group" as used herein means an —S-alkyl group, wherein alkyl is as defined above such as meththio, eththio, n-propylthio, i-propylthio, n-butylthio, i-butylthio, t-butylthio, pentylthio including their isomers.

The term "haloalkoxy group" as used herein means an —O-haloalkyl group, wherein haloalkyl is as defined above. Examples of haloalkoxy groups include, but are not limited to, 2,2,2-trifluoroethoxy, difluoromethoxy and 1,1,1,3,3,3-hexafluoro-iso-propoxy.

The term "haloalkthio group" as used herein means an —S-haloalkyl group, wherein haloalkyl is as defined above. An example of haloalkthio groups includes, but are not limited to, 2,2,2-trifluoroethththanthiol.

The term "aryloxy group" as used herein means an O-aryl group wherein aryl is as defined above. An aryloxy group can be unsubstituted or substituted with one or more suitable substituents. Preferably, the aryl ring of an aryloxy group is a monocyclic ring, wherein the ring comprises 6 carbon atoms, referred to herein as "$(C_6)$ aryloxy". The term "optionally substituted aryloxy" means the aryl or group may be substituted with one to three groups selected from the group consisting of $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfmyl, $C_{1-6}$ alkylsulfonyl, $C_{1-6}$ haloalkoxy, $C_{1-6}$ haloalkylthio, halogen, amino, alkylamino, dialkylamino, aminoacyl, acyl, alkoxycarbonyl, carbamoyl, N-alkylcarbamoyl, N,N-dialkylcarbamoyl, nitro and cyano.

The term "heteroaryloxy group" as used herein means an O-heteroaryl group, wherein heteroaryl is as defined above. The heteroaryl ring of a heteroaryloxy group can be unsubstituted or substituted with one or more suitable substituents. Examples of heteroaryl groups include, but are not limited to, 2-pyridyloxy, 3-pyrrolyloxy, 3-pyrazolyloxy, 2-imidazolyloxy, 3-pyrazinyloxy, and 4-pyrimidyloxy.

The term "acyl" or "alkylcarbonyl" as used herein denotes a radical of formula $C(=O)R$ wherein R is hydrogen, unbranched or branched alkyl containing 1 to 6 carbon atoms or a phenyl group.

The term "alkoxycarbonyl" as used herein denotes a radical of formula $C(=O)OR$ wherein R is, unbranched or branched alkyl as described above.

The term "acylamino" as used herein denotes a radical of formula —NH-(acyl) where acyl is as defined herein.

The term "arylboronic acid" as used herein denotes a radical of formula $ArB(OH)_2$ wherein Ar is an optionally substituted aryl group as described above.

The term "alkylene" as used herein denotes a divalent linear or branched saturated hydrocarbon radical, having from one to six carbons inclusive, unless otherwise indicated. Examples of alkylene radicals include, but are not limited to, methylene, ethylene, propylene, 2-methyl-propylene, butylene, 2-ethylbutylene.

The term "arylalkyl" or "aralkyl" as used herein denotes the radical R'R"—, wherein R' is an aryl radical as defined herein, and R" is an alkylene radical as defined herein and the arylalkyl group is attached through the alkylene radical. Examples of arylalkyl radicals include, but are not limited to, benzyl, phenylethyl, 3-phenylpropyl.

The term "halogen" as used herein means fluorine, chlorine, bromine, or iodine. Correspondingly, the meaning of the term "halo" encompasses fluoro, chloro, bromo, and iodo. The term "hydrohalic acid" refers to an acid comprised of hydrogen and a halogen.

The term "alkylsulfinyl" as used herein means the radical —S(O)R', wherein R' is alkyl as defined herein. Examples of alkylaminosulfonyl include, but are not limited to methylsulfinyl and iso-propylsulfinyl.

The term "alkylsulfonyl" as used herein means the radical —$S(O)_2R'$, wherein R' is alkyl as defined herein. Examples of alkylaminosulfonyl include, but are not limited to methylsulfonyl and iso-propylsulfonyl.

The terms "amino", "alkylamino" and "dialkylamino" as used herein refer to —$NH_2$, —NHR and —$NR_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to $NH_2(CH_2)n$-, $RHN(CH_2)n$-, and $R_2N(CH_2)n$- respectively wherein n is 1 to 6 and R is alkyl as defined above The prefix "carbamoyl" as used herein means the radical —$CONH_2$. The prefix "N-alkylcarbonyl" and "N,N-dialkylcarbamoyl" means a radical CONHR' or CONR'R" respectively wherein the R' and R" groups are independently alkyl as defined herein.

The term "conjugate base" as used herein means the chemical species produced when an acid (including here a carbon acid) gives up its proton.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH—⇌—C(—OH)=CH—), amide/imidic acid (—C(=O)—NH—⇌—C(—OH)=N—) and amidine (—C(=NR)—NH—⇌—C(—NHR)=N—) tautomers. The latter two are particularly common in heteroaryl and heterocyclic rings and the present invention encompasses all tautomeric forms of the compounds.

Compounds of formula I which are basic can form pharmaceutically acceptable acid addition salts with inorganic acids such as hydrohalic acids (e.g. hydrochloric acid and hydrobromic acid), sulphuric acid, nitric acid and phosphoric acid, and the like, and with organic acids (e.g. with acetic acid, tartaric acid, succinic acid, fumaric acid, maleic acid, malic acid, salicylic acid, citric acid, methanesulphonic acid and p-toluenesulfonic acid, and the like).

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "hydrate" as used herein means a compound of the invention or a salt thereof, that further includes a stoichiometric or non-stoichiometric amount of water bound by non-covalent intermolecular forces.

The term "clathrate" as used herein means a compound of the invention or a salt thereof in the form of a crystal lattice that contains spaces (e. g., channels) that have a guest molecule (e. g., a solvent or water) trapped within.

The term "nucleoside and nucleotide reverse transcriptase inhibitors" ("NRTI's) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR tradename; didanosine (ddI) available under the VIDEX tradename.; zalcitabine (ddC) available under the HIVID tradename; stavudine (d4T) available under the ZERIT trademark.; lamivudine (3TC) available under the EPIVIR tradename; abacavir (1592U89) disclosed in WO96/30025 and available under the ZIAGEN trademark; adefovir dipivoxil [bis(POM)-PMEA] available under the PREVON tradename; lobucavir (BMS-180194), a nucleoside reverse transcriptase inhibitor disclosed in EP-0358154 and EP-0736533 and under development by Bristol-Myers Squibb; BCH-10652, a reverse transcriptase inhibitor (in the form of a racemic mixture of BCH-10618 and BCH-10619) under development by Biochem Pharma; emitricitabine [(−)-FTC] licensed from Emory University under U.S. Pat. No. 5,814,639 and under development by Triangle Pharmaceuticals; beta-L-FD4 (also called beta-L-D4C and named beta-L-2', 3'-dicleoxy-5-fluoro-cytidene) licensed by Yale University to Vion Pharmaceuticals; DAPD, the purine nucleoside, (−)-beta-D-2,6,-diamino-purine dioxolane disclosed in EP-0656778 and licensed to Triangle Pharmaceuticals; and lodenosine (FddA), 9-(2,3-dideoxy-2-fluoro-b-D-threo-pentofturanosyl)adenine, an acid stable purine-based reverse transcriptase inhibitor discovered by the NIH and under development by U.S. Bioscience Inc.

The term "non-nucleoside reverse transcriptase inhibitors" ("NNRTI's") as used herein means non-nucleosides that inhibit the activity of HIV-1 reverse transcriptase.

Typical suitable NNRTIs include nevirapine (BI-RG-587) available under the VIRAMUNE tradename; delaviradine (BHAP, U-90152) available under the RESCRIPTOR tradename; efavirenz (DMP-266) a benzoxazin-2-one disclosed in WO94/03440 and available under the SUSTIVA tradename; PNU-142721, a furopyridine-thio-pyrimide; AG-1549 (formerly Shionogi # S-1153); 5-(3,5-dichlorophenyl)-thio-4-isopropyl-1-(4-pyridyl)methyl-1H-imidazol-2-ylmethyl carbonate disclosed in WO 96/10019; MKC-442 (1-(ethoxy-methyl)-5-(1-methylethyl)-6-(phenylmethyl)-(2,4(1H,3H)-pyrimidinedione); and (+)-calanolide A (NSC-675451) and B, coumarin derivatives disclosed in U.S. Pat. No. 5,489,697

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual finctional proteins found in infectious HIV-1. HIV protease inhibitors include compounds having a peptidomimetic structure, high molecular weight (7600 daltons) and substantial peptide character, e.g. CRIXIVAN as well as non-peptide protease inhibitors e.g., VIRACEPT.

Typical suitable PIs include saquinavir available in hard gel capsules under the INVIRASE tradename and as soft gel capsules under the FORTOVASE tradename; ritonavir (ABT-538) available under the NORVIR tradename; indinavir (MK-639) available under the CRIXIVAN tradename; nelfnavir (AG-1343) available under the VIRACEPT; amprenavir (141 W94), tradename AGENERASE, a non-peptide protease inhibitor; lasinavir (BMS-234475; originally discovered by Novartis, Basel, Switzerland (CGP-61755); DMP-450, a cyclic urea discovered by Dupont; BMS-2322623, an azapeptide under development by Bristol-Myers Squibb, as a 2nd-generation HIV-1 PI; ABT-378; AG-1549 an orally active imidazole carbamate.

Other antiviral agents include hydroxyurea, ribavirin, IL-2, IL-12, pentafuside and Yissum Project No. 11607. Hydroxyurea (Droxia), a ribonucleoside triphosphate reductase inhibitor, the enzyme involved in the activation of T-cells. Hydroxyurea was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN (aldesleukin) tradename as a lyophilized powder for IV infusion or sc administration upon reconstitution and dilution with water; a dose of about 1 to about 20 million 1 U/day, sc is preferred; a dose of about 15 million 1 U/day, sc is more preferred. IL-12 is disclosed in WO96/25171 and is available as a dose of about 0.5 microgram/kg/day to about 10 microgram/kg/day, sc is preferred. Pentafuside (DP-178, T-20) a 36-amino acid synthetic peptide, disclosed in U.S. Pat. No. 5,464,933 and available under the FUZEON tradename; pentafuside acts by inhibiting fusion of HIV-1 to target membranes. Pentafliside (3-100 mg/day) is given as a continuous sc infusion or injection together with efavirenz and 2 PI's to HIV-1 positive patients refractory to a triple combination therapy; use of 100 mg/day is preferred. Yissum Project No. 11607, a synthetic protein based on the HIV-1 Vif protein. Ribavirin, 1-.beta.-D-ribofaranosyl-1H-1,2,4-triazole-3-carboxamide, is described in U.S. Pat. No. 4,211,771.

The term "anti-HIV-1 therapy" as used herein means any anti-HIV-1 drug found usefull for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include:

(a) triple combination therapies such as two NRTIs and one PI; or (b) two NRTIs and one NNRTI; and (c) quadruple combination therapies such as two NRTIs, one PI and a second PI or one NNRTI. In treatment of naive patients, it is preferred to start anti-HIV-1 treatment with the triple combination therapy; the use of two NRTIs and one PI is preferred unless there is intolerance to PIs. Drug compliance is essential. The CD4.sup.+ and HIV-1-RNA plasma levels should be monitored every 3-6 months. Should viral load plateau, a fourth drug, e.g., one PI or one NNRTI could be added.

The term "wild type" as used herein refers to the HIV virus strain which possesses the dominant genotype which naturally occurs in the normal population which has not been exposed to reverse transcriptase inhibitors. The term "wild type reverse transcriptase" used herein has refers to the reverse transcriptase expressed by the wild type strain which has been sequenced and deposited in the SwissProt database with an accession number P03366.

The term "reduced susceptibility" as used herein refers to about a 10 fold, or greater, change in sensitivity of a particular viral isolate compared to the sensitivity exhibited by the wild type virus in the same experimental system

ABBREVIATIONS

The following abbreviations are used throughout this application and they have the meaning listed below:

| | |
|---|---|
| AIBN | azo-bis-isobutyrylnitrile |
| atm | atmospheres |
| BBN or 9-BBN | 9-borabicyclo[3.3.1]nonane |
| Boc | tert-butoxycarbonyl |
| BOC$_2$O | Di-tert-butyl pyrocarbonate or boc anhydride |
| Bn | benzyl |
| cbz or Z | benzyloxycarbonyl |
| DABCO | diazabicyclooctane |
| DAST | diethylaminosulfur trifluoride |
| DCE | 1,2-dichloroethane |
| DCM | dichloromethane |
| DEAD | diethyl azodicarboxylate |
| DIAD | di-iso-propylazodicarboxylate |
| DIBAL-H | di-iso-butylaluminumhydride |
| DMA | N,N-dimethyl acetamide |
| DMAP | 4-N,N-dimethylaminopyridine |
| DMF | N,N-dimethylformamide |
| dppf | 1,1'-Bis(diphenylphosphino)ferrocene |
| EDCI | 1-(3-dimethylaminopropyl)-3-ethylcarbodiimide hydrochloride |
| EtOAc | ethyl acetate |
| Et$_2$O | diethyl ether |
| Et | ethyl |
| EtOH | ethanol |
| LAH | lithium aluminum hydride |
| LiHMDS | lithium hexamethyl disilazane |
| h | hour(s) |
| HOAc | acetic acid |
| i-Pr | iso-propyl |
| m | minute(s) |
| Me | methyl |
| MeCN | acetonitrile |
| MeOH | methanol |
| MTBE | methyl t-butyl ether |
| NBS | N-bromosuccinimide |
| NMP | N-methylpyrrolidone |
| PCC | pyridinium chlorochromate |
| PDC | pyridinium dichromate |
| psi | pounds per square inch |
| pyr | pyridine |
| rt or RT | room temperature |
| TEA or Et$_3$N | triethylamine |
| Tf | triflate CF$_3$SO$_2$— |
| TFA | trifluoroacetic acid |
| THF | tetrahydrofuran |
| TLC | thin layer chromatography |
| TMHD | 2,2,6,6-tetramethylheptane-2,6-dione |
| TsOH | p-toluenesulfonic acid |

EXAMPLES OF COMPOUNDS representative examples of [3-phenoxybenzyl]pyridazinones within the scope of the invention are provided in the following table. These examples and preparations are provided to enable those skilled in the art to more clearly understand and to practice the present invention. In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight.

TABLE I

| cpd # | Structure | Name | [M + H]$^+$ (mw) mp |
|---|---|---|---|
| I-1 | 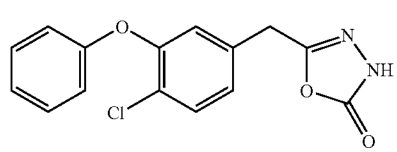 | 5-(4-Chloro-3-phenoxy-benzyl)-3H-[1,3,4]oxadiazol-2-one | (302.7195) |
| I-2 | 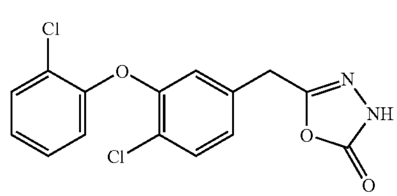 | 5-[4-Chloro-3-(2-chloro-phenoxy)-benzyl]-3H-[1,3,4]oxadiazol-2-one | (337.1646) |
| I-3 | 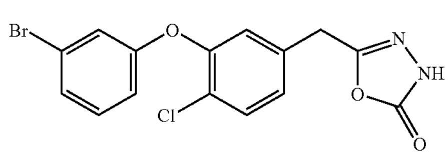 | 5-[3-(3-Bromo-phenoxy)-4-chloro-benzyl]-3H-[1,3,4]oxadiazol-2-one | (381.6156) |

TABLE I-continued

| cpd # | Structure | Name | [M + H]+ (mw) mp |
|---|---|---|---|
| I-4 | 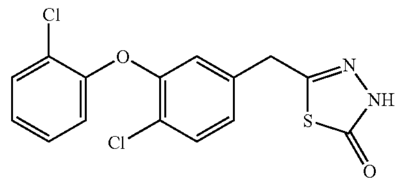 | 5-[4-Chloro-3-(2-chloro-phenoxy)-benzyl]-3H-[1,3,4]thiadiazol-2-one | (353.2292) |
| I-5 | 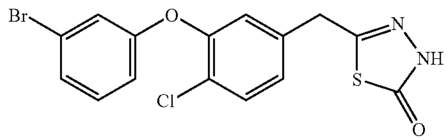 | 5-[3-(3-Bromo-phenoxy)-4-chloro-benzyl]-3H-[1,3,4]thiadiazol-2-one | (397.6802) |
| I-6 | 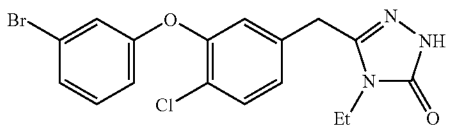 | 5-[3-(3-Bromo-phenoxy)-4-chloro-benzyl]-4-ethyl-2,4-dihydro-[1,2,4]triazol-3-one | 408 (408.685) |
| I-7 | 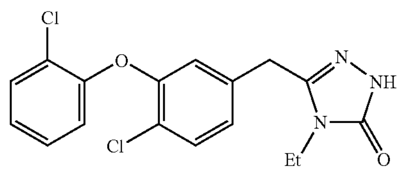 | 5-[4-Chloro-3-(2-chloro-phenoxy)-benzyl]-4-ethyl-2,4-dihydro-[1,2,4]triazol-3-one | 364 (364.234) |
| I-8 | 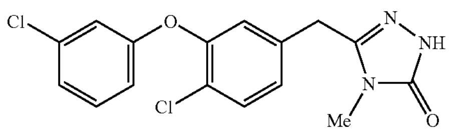 | 5-[4-Chloro-3-(3-chloro-phenoxy)-benzyl]-4-methyl-2,4-dihydro-[1,2,4,]triazol-3-one | 350 (350.2069) |
| I-9 | 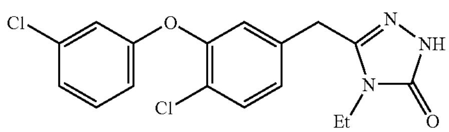 | 5-[4-Chloro-3-(3-chloro-phenoxy)-benzyl]-4-ethyl-2,4-dihydro-[1,2,4]triazol-3-one | 364 (364.23) |
| I-10 | 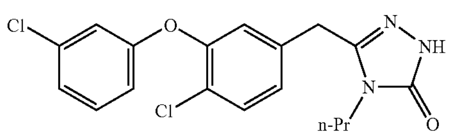 | 5-[4-Chloro-3-(3-chloro-phenoxy)-benzyl]-4-propyl-2,4-dihydro-[1,2,4]triazol-3-one | 378 (378.26) |
| I-11 | 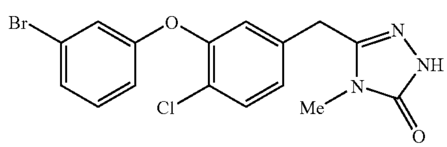 | 5-[3-(3-Bromo-phenoxy)-4-chloro-benzyl]-4-methyl-2,4-dihydro-[1,2,4]triazol-3-one | 394 (394.65) |
| I-12 | 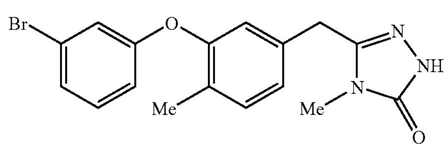 | 5-[3-(3-Bromo-phenoxy)-4-methyl-benzyl]-4-methyl-2,4-dihydro-[1,2,4]triazol-3-one | 374 (374.23) |
| I-13 | 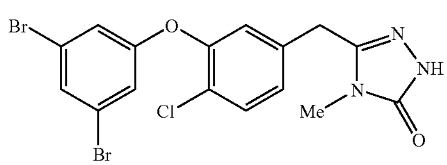 | 5-[4-Chloro-3-(3,5-dibromo-phenoxy)-benzyl]-4-methyl-2,4-dihydro-[1,2,4]triazol-3-one | 473.55 (474) |

TABLE I-continued

| cpd # | Structure | Name | [M + H]+ (mw) mp |
|---|---|---|---|
| I-14 | 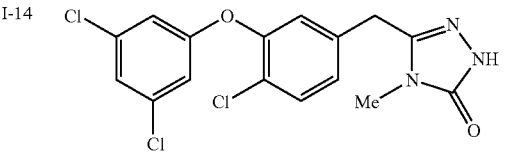 | 5-[4-Chloro-3-(3,5-dichloro-phenoxy)-benzyl]-4-methyl-2,4-dihydro-[1,2,4]triazol-3-one | 402.64 (404) |
| I-15 | 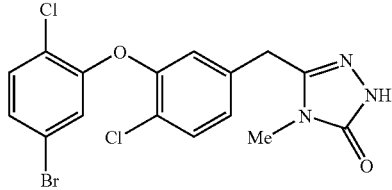 | 5-[3-(5-Bromo-2-chloro-phenoxy)-4-chloro-benzyl]-4-methyl-2,4-dihydro-[1,2,4]triazol-3-one | 430 (429.1) |
| I-16 | 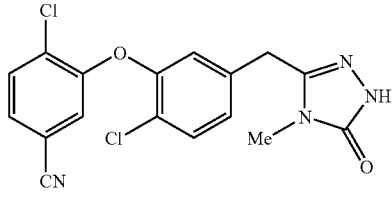 | 4-Chloro-3-[2-chloro-5-(4-methyl-5-oxo-4,5-dihydro-1H-[1,2,4]triazol-3-ylmethyl)-phenoxy]-benzonitrile | 375 (375.21) |
| I-17 | 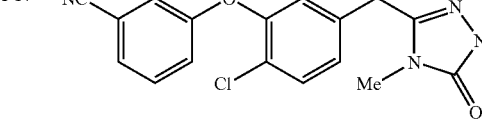 | 3-[2-Chloro-5-(4-methyl-5-oxo-4,5-dihydro-1H-[1,2,4]triazol-3-ylmethyl)-phenoxy]-benzonitrile | 341 (340.77) |
| I-18 | 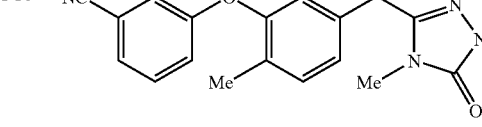 | 3-[2-Methyl-5-(4-methyl-5-oxo-4,5-dihydro-1H-[1,2,4]triazol-3-ylmethyl)-phenoxy]-benzonitrile | 321 (320.35) |
| I-19 | 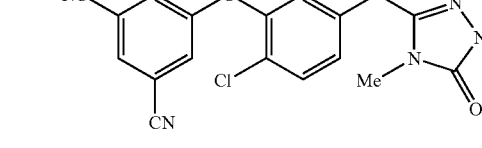 | 5-[2-Chloro-5-(4-methyl-5-oxo-4,5-dihydro-1H-[1,2,4]triazol-3-ylmethyl)-phenoxy]-isophthalonitrile | 366 (365.78) 217.8–219.1 |
| I-20 | 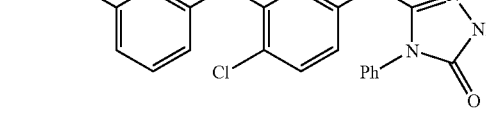 | 5-[4-Chloro-3-(3-chloro-phenoxy)-benzyl]-4-phenyl-2,4-phenyl-2,4-dihydro-[1,2,4]triazol-3-one | 412 (412.27) |
| I-21 | 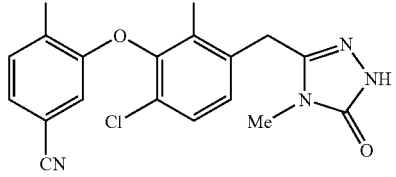 | 4-Chloro-3-[6-chloro-2-fluoro-3-(4-methyl-5-oxo-4,5-dihydro-1H-[1,2,4]triazol-3-ylmethyl)-phenoxy]-benzonitrile | 393 (393.2) |

TABLE I-continued

| cpd # | Structure | Name | [M + H]+ (mw) mp |
|---|---|---|---|
| I-22 | 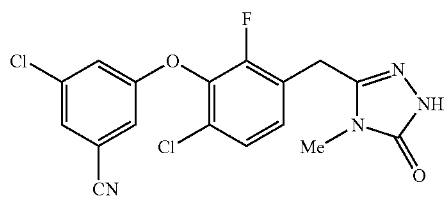 | 3-Chloro-5-[6-chloro-2-fluoro-3-(4-methyl-5-oxo-4,5-dihydro-1H-[1,2,4]triazol-3-ylmethyl)-phenoxy]-benzonitrile | 447 (447.09) 167.8-171.2 |
| I-23 | 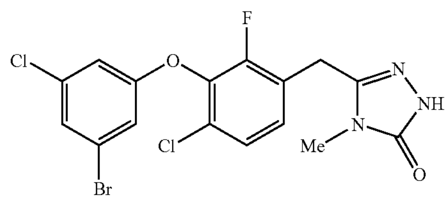 | 5-[3-(3-Bromo-5-chloro-phenoxy)-4-chloro-2-fluoro-benzyl]-4-methyl-2,4-dihydro-[1,2,4]triazol-3-one | 447 (447.09) 212.3-215.8 |
| I-24 | 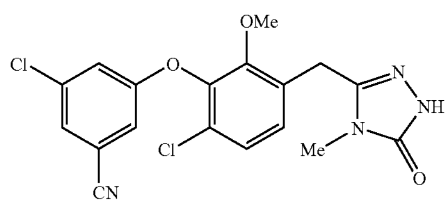 | 3-Chloro-5-[6-chloro-2-methoxy-3-(4-methyl-5-oxo-4,5-dihydro-1H-[1,2,4]triazol-3-ylmethyl)-phenoxy]-benzonitrile | 405 (405.24) 194.4-198.6 |
| I-25 | 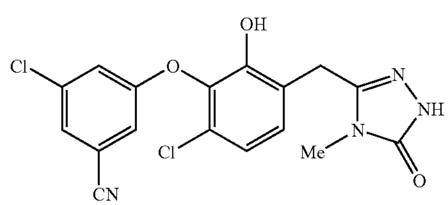 | 3-Chloro-5-[6-chloro-2-hydroxy-3-(4-methyl-5-oxo-4,5-dihydro-1H-[1,2,4]triazol-3-ylmethyl)-phenoxy]-benzonitrile | 391 (391.21) 185-186.2 |
| I-26 | 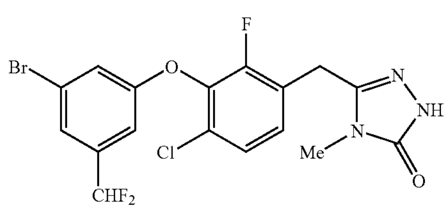 | 5-[4-Chloro-3-(3-chloro-5-difluoromethyl-phenoxy)-2-fluoro-benzyl]-4-methyl-2,4-dihydro-[1,2,4]triazol-3-one | 461 (461) 180.6-185.2 |
| I-27 | 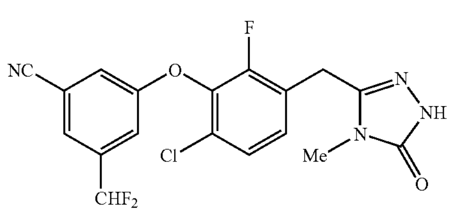 | 3-[6-Chloro-2-fluoro-3-(4-methyl-5-oxo-4,5-dihydro-1H-[1,2,4]triazol-3-ylmethyl)-phenoxy]-5-difluoromethyl-benzonitrile | 408 (408.77) 190.7-192.8 |
| I-28 | 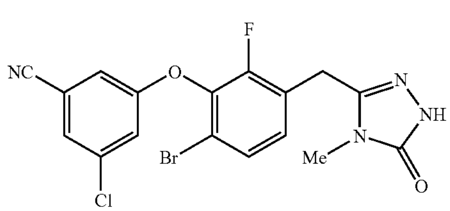 | 3-[6-Bromo-2-fluoro-3-(4-methyl-5-oxo-4,5-dihydro-1H-[1,2,4]triazol-3-ylmethyl)-phenoxy]-5-chloro-benzonitrile | 436 (437.66) 188-190 |

TABLE I-continued

| cpd # | Structure | Name | [M + H]+ (mw) mp |
|---|---|---|---|
| I-29 | 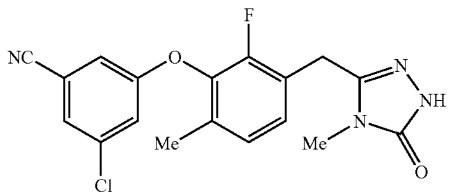 | 3-[6-Bromo-2-fluoro-3-(4-methyl-5-oxo-4,5-dihydro-1H-[1,2,4]triazol-3-ylmethyl)-phenoxy]-5-chloro-benzonitrile | 372 (372.79) 198.6-201.9 |
| I-30 | 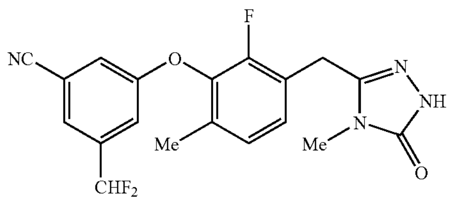 | 3-Difluoromethyl-5-[2-fluoro-6-methyl-3-(4-methyl-5-oxo-4,5-dihydro-1H-[1,2,4]triazol-3-ylmethyl)-phenoxy]-benzonitrile | (388.35) |
| I-31 | 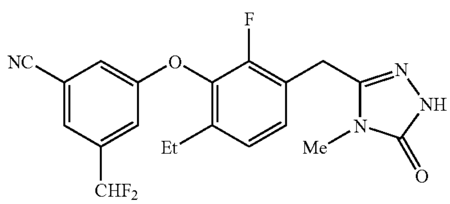 | 3-Difluoromethyl-5-[2-fluoro-6-methyl-3-(4-ethyl-5-oxo-4,5-dihydro-1H-[1,2,4]triazol-3-ylmethyl)-phenoxy]-benzonitrile | (402.38) |
| I-32 | 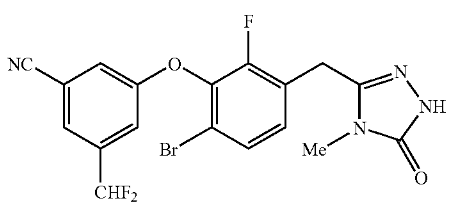 | 3-[6-Bromo-2-fluoro-3-(4-methyl-5-oxo-4,5-dihydro-1H-[1,2,4]triazol-3-ylmethyl)-phenoxy]-5-difluoromethyl-benzonitril | (453.22) |
| I-33 | 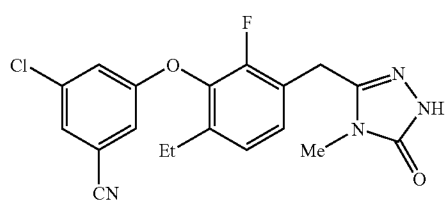 | 3-Chloro-5-[6-ethyl-2-fluoro-3-(4-methyl-5-oxo-4,5-dihydro-1H-[1,2,4]triazol-3-ylmethyl)-phenoxy]-benzonitrile | (386.82) |
| I-34 | 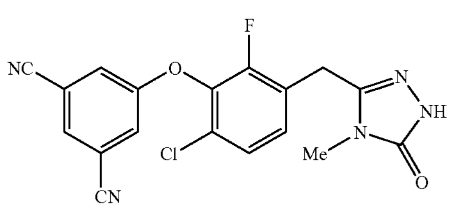 | 5-[6-Chloro-2-fluoro-3-(4-methyl-5-oxo-4,5-dihydro-1H-[1,2,4]triazol-3-ylmethyl)-phenoxy]-isophthalonitrile | (383.77) |
| I-35 | 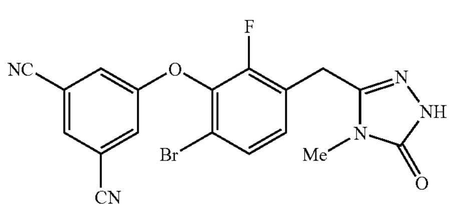 | 5-[6-Bromo-2-fluoro-3-(4-methyl-5-oxo-4,5-dihydro-1H-[1,2,4]triazol-3-ylmethyl)-phenoxy]-isophthalonitrile | (428.22) |

TABLE I-continued

| cpd # | Structure | Name | [M + H]+ (mw) mp |
|---|---|---|---|
| I-36 | ![structure] | 5-[2-Fluoro-6-methyl-3-(4-methyl-5-oxo-4,5-dihydro-1H-[1,2,4]triazol-3-ylmethyl)-phenoxy]-isophthalonitrile | (363.35) |
| I-37 | ![structure] | 5-[6-Ethyl-2-fluoro-3-(4-methyl-5-oxo-4,5-dihydro-1H-[1,2,4]triazol-3-ylmethyl)-phenoxy]-isophthalonitrile | (377.38) |

Preparation of Compounds of the Invention

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes and examples are merely illustrative of some methods by which the compounds of the present invention can be synthesized, and various modifications to these synthetic reaction schemes can be made and will be suggested to one skilled in the art having referred to the disclosure contained in this Application.

The heterocyclic compounds of the present invention are prepared by a two-stage process (Scheme 1) comprising construction of an appropriately substituted aryl ring 2 and subsequently introducing the heterocyclic ring 3. Although stages can be accomplished in any order, the heterocyclic ring is generally introduced after the modifications of the aryl ring are completed. Substituted alkyl m-hydroxyphenylacetate 1a or m-hydroxyphenylacetonitrile 1b derivatives are convenient starting materials. They are often commercially available or readily prepared from commercially available precursors. Alternatively the aryl ring may be substituted with a methyl 1c or carboxylic acid ester 1d substituent which is subsequently converted to 1b (for example, see schemes 4 and 5). One skilled in the art will also appreciate the substituents can altered after introduction of the heterocyclic ring.

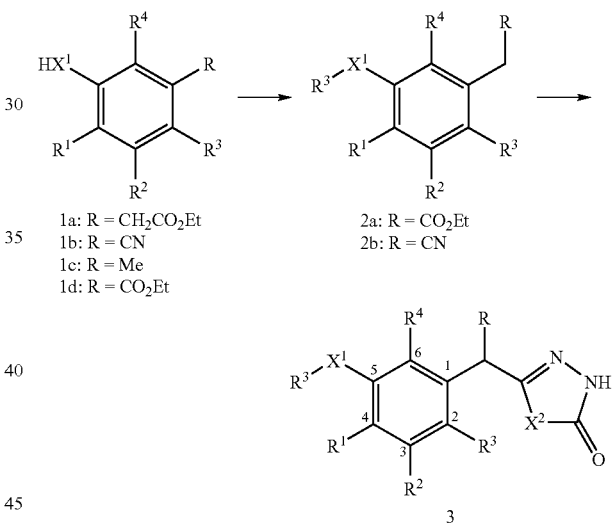

SCHEME 1

1a: R = CH$_2$CO$_2$Et
1b: R = CN
1c: R = Me
1d: R = CO$_2$Et

2a: R = CO$_2$Et
2b: R = CN

3

Preparation of Phenylacetic Acid and Phenylacetonitile Precursors (Scheme 1)

Ethyl 3-hydroxy4-methylphenylacetate (5a) was prepared from ethyl 3-methoxy-4-hydroxy-phenylacetate as shown in Scheme 2. The phenol was converted to the triflate ester 4b which was subjected to displacement with Me$_2$Zn, DIBAL-H and PdCl$_2$(dppf) (E.-i. Negishi in *Metal-catalyzed Cross-Coupling Reactions*, F. Diederich and P. J. Stang (eds.), Wiley-VCH, Mannheim 1998, chap. 1; E. Erdik, *Tetrahedron* 1992 48:9577-9648) to afford the 4c. Boron tribromide demethylation afforded 5a. Ethyl 3-hydroxy-4-ethylphenylacetate 5b was prepared by Friedel-Crafts acylation of 4d which afforded ethyl 4-acetyl-3-methoxyphenylacetate (4e). Reduction of the ketone with triethylsilane and TFA produced the corresponding 4-ethyl substituted derivative 4f which was demethylated with BBr$_3$ to afford 5b. Ethyl 3-hydroxy-4-iso-propylphenylacetate (5c) was prepared by Wittig olefmation of 4e and subsequent catalytic hydrogenation of the 2-propenyl substituent to yield 4h. Demethylation with boron tribromide produced 5c.

SCHEME 2

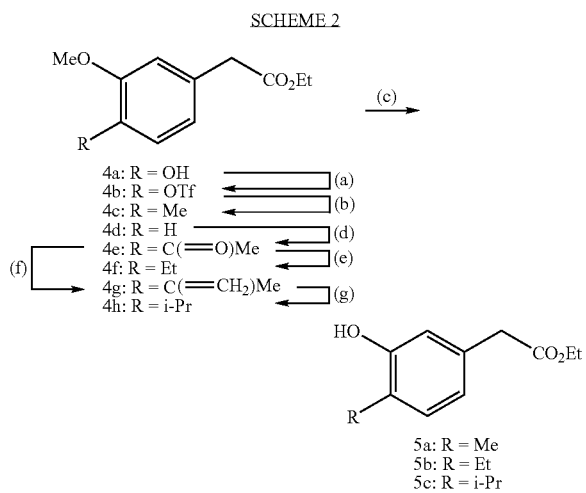

4a: R = OH
4b: R = OTf
4c: R = Me
4d: R = H
4e: R = C(═O)Me
4f: R = Et
4g: R = C(═CH₂)Me
4h: R = i-Pr

5a: R = Me
5b: R = Et
5c: R = i-Pr (a) (CF₃SO₂)₂O, Pyr, CH₂Cl₂; (b) ZnMe₂, PdCl₂(dppf), DIBAL-H, 0° to Δ;
(c) BBr₃, CH₂Cl₂, -78° C.; (d) MeCOCl, SnCl₄, CH₂Cl₂; (e) Et₃SiH, TFA;
(f) MePPh₃⁺ Cl⁻, n-BuLi, THF; (e) H₂, Pd/C, EtOH Ethyl 3,4-dimethyl-5-hydroxyphenylacetate (8) was prepared by formylation of 6a and esterification of the resulting carboxylic acid 6b to produce ethyl 3-formyl4-hydroxy-5-methoxyphenyl acetate (7a). Reduction of the aldehyde and hydrogenolysis the resulting benzyl alcohol afforded 7b. The second methyl substituent was introduced by sequential treatment of 7b with triflic anhydride which yielded 7c and displacement with Me₂Zn, PdCl₂(dppf) and DIBAL-H (supra) to produce 7c. Boron tribromide mediated demethylation afforded 8. (Scheme 3)

SCHEME 3

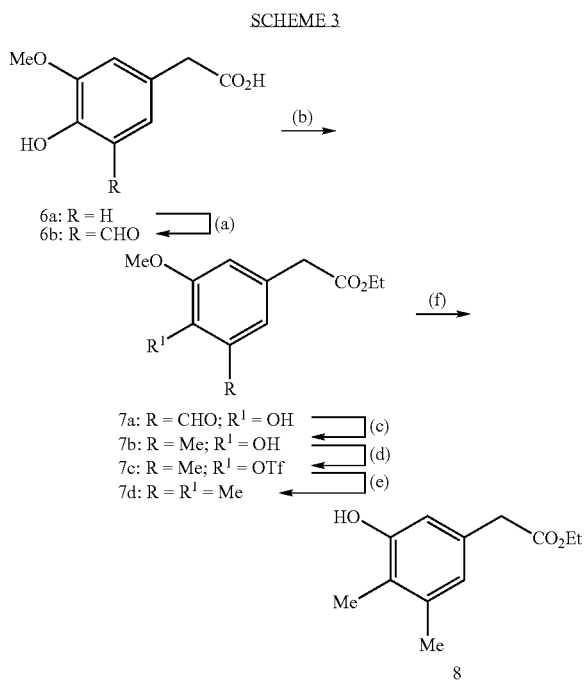

6a: R = H
6b: R = CHO

7a: R = CHO; R¹ = OH
7b: R = Me; R¹ = OH
7c: R = Me; R¹ = OTf
7d: R = R¹ = Me (a) hexamethylene tetraamine, TFA; (b) EtOH, H₂SO₄; (c) H₂, Pd/C, HOAc;
(d) Tf₂O, pyr, CH₂Cl₂; (e) Me₂Zn, PdCl₂(prof), DIBAL-H; (f) BBr₃, CH₂Cl₂, -78° C.

Ethyl 4-chloro-3-hydroxyphenyl acetate (10) was prepared from 4-chloro-3-methoxytoluene by sequential free radical bromination (9b), nucleophilic displacement of the bromine atom with cyanide (9c) and a two-step hydrolysis of the nitrile to the amidine hydrochloride 9d and subsequently to the ethyl ester 9e. Boron tribromide mediated demethylation as described previously afforded 10. (Scheme 4)

SCHEME 4

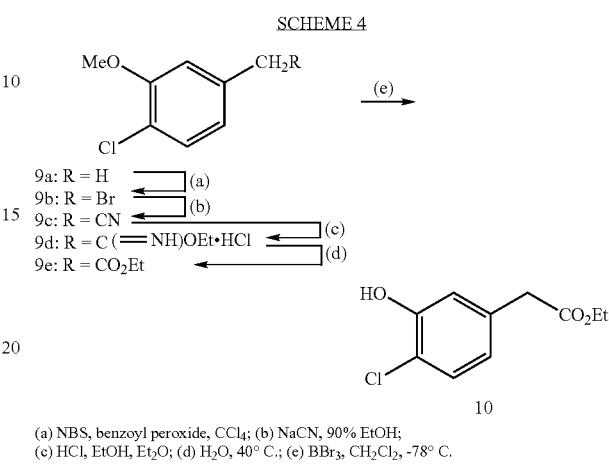

9a: R = H
9b: R = Br
9c: R = CN
9d: R = C(═NH)OEt·HCl
9e: R = CO₂Et (a) NBS, benzoyl peroxide, CCl₄; (b) NaCN, 90% EtOH;
(c) HCl, EtOH, Et₂O; (d) H₂O, 40° C.; (e) BBr₃, CH₂Cl₂, -78° C.

6-Methyl derivatives were prepared from 3-hydroxy-2-methylbenzoic acid (11) which was chlorinated (NaOCl/NaOH) and esterified to afford 13. Cupric acetate mediated coupling (infra) of benzeneboronic acid provided the diaryl ether 14. The nitrile was introduced by sequential reduction, mesylation and cyanide displacement to afford 17. The mesylate underwent an in situ displacement by chloride during the mesylation reaction.

SCHEME 5

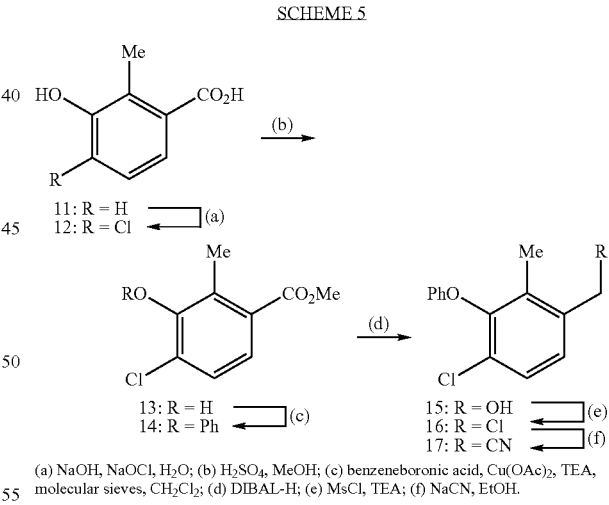

11: R = H
12: R = Cl

13: R = H
14: R = Ph

15: R = OH
16: R = Cl
17: R = CN (a) NaOH, NaOCl, H₂O; (b) H₂SO₄, MeOH; (c) benzeneboronic acid, Cu(OAc)₂, TEA, molecular sieves, CH₂Cl₂; (d) DIBAL-H; (e) MsCl, TEA; (f) NaCN, EtOH.

6-fluoro- and chloro- derivatives were available from 6-chloro-2-fluoro-3-methylphenol (18) and 3-bromo-2,4-dichlorotoluene (19), respectively (Scheme 6). The base-catalyzed reaction of 18 and p-fluoro-nitrobenzene yielded dairyl ether 20. Conversion of the nitro substiuent to the corresponding amine followed by diazotization and reduction produced 4-chloro-2-fluoro-3-phenoxytoluene (22). One skilled in the art will appreciate that the availability of amino-substituted aryl groups affords the possibility to replace the amino substiuent with a variety of other substituents utilizing the Sandmeyer reaction. Cupric chloride-mediated coupling (see infra) of 19 afforded the corresponding 2,4-dichloro-3-phenoxytoluene (23). Elaboration of the acetonitrile sidechain in 24 and 25 was accomplished by benzylic bromination and displacement.

SCHEME 6

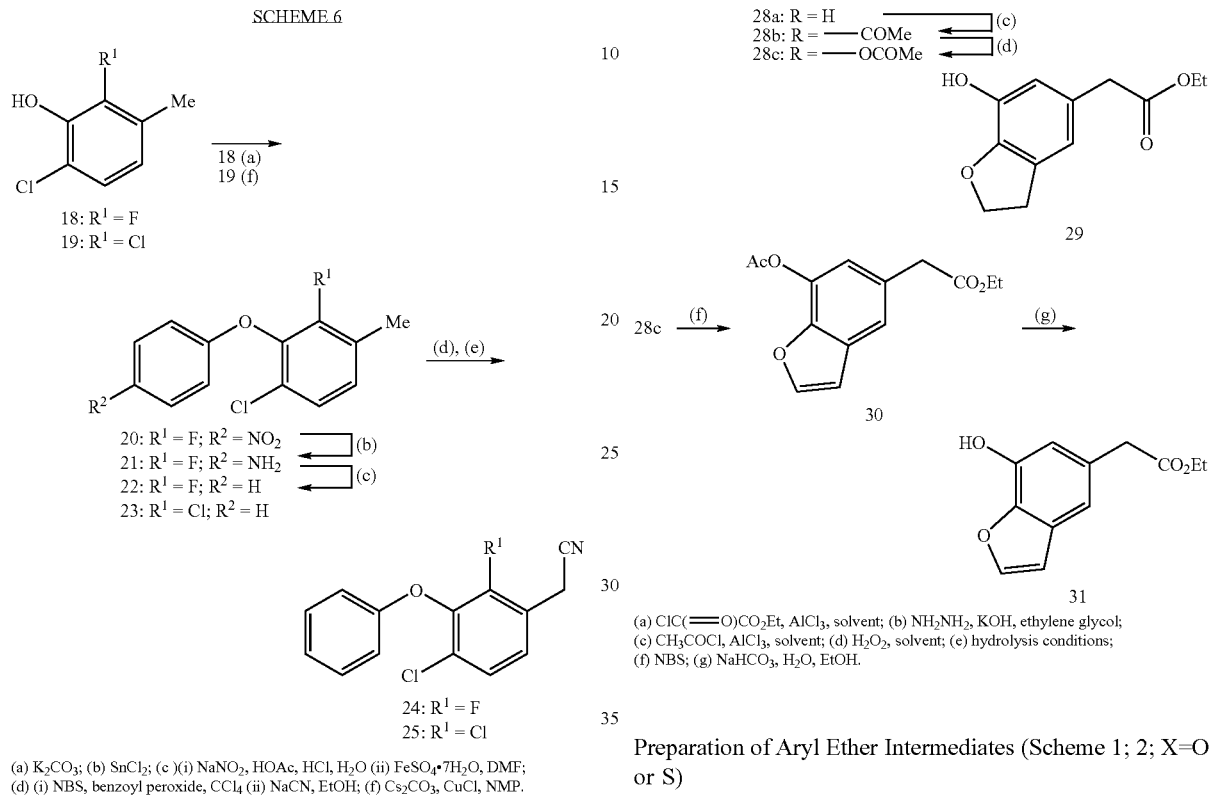

(a) K₂CO₃; (b) SnCl₂; (c)(i) NaNO₂, HOAc, HCl, H₂O (ii) FeSO₄·7H₂O, DMF; (d) (i) NBS, benzoyl peroxide, CCl₄ (ii) NaCN, EtOH; (f) Cs₂CO₃, CuCl, NMP.

Benzofuran 31 and dihydrobenzofuran 29 derivatives (Scheme 7) were prepared from dihydrobenzofuran (26). Acylation with ethyl chloro oxalate produced the α-ketoester 27 which was reduced to the corresponding phenylacetic acid derivative 28a under Wolff-Kischner conditions. The preparation of 29 by a Wilgerodt reaction also has been reported (J. Dunn et al. *J. Med Chem* 1986 29:2326). Freidel-Crafts acylation with acetyl chloride afforded the acetyl derivative 28b which was converted to the acetate 28c under Baeyer-Villiger conditions and subsequently hydrolyzed to 29. The corresponding benzofuran analogs were prepared by benzylic bromination and concomitant dehydrohalogention to yield 31.

SCHEME 7

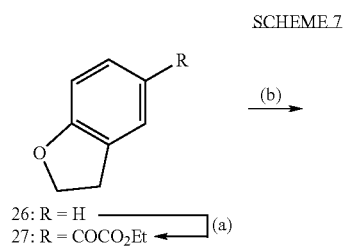

(a) ClC(=O)CO₂Et, AlCl₃, solvent; (b) NH₂NH₂, KOH, ethylene glycol; (c) CH₃COCl, AlCl₃, solvent; (d) H₂O₂, solvent; (e) hydrolysis conditions; (f) NBS; (g) NaHCO₃, H₂O, EtOH.

Preparation of Aryl Ether Intermediates (Scheme 1; 2; X=O or S)

The preparation of diaryl ethers has been reviewed (J. S. Sawyer, *Recent Advances in Diaryl Ether Synthesis, Tetrahedron* 2000 56:5045-5065). The diaryl ethers required herein were prepared by three different methods (Scheme 8): (i) Cu(OAc)₂ catalyzed condensation of substituted benzene boronic acids and phenols (D. A. Evans et al., *Synthesis of Diaryl Ethers through the Copper-Promoted Arylation of Phenols with Aryl Boronic Acids. An Expedient Synthesis of Thyroxine, Tetrahedron Lett.*, 1998 39:2937-2940 and D. M. T. Chan et al., *New N- and O-Arylations with Phenylboronic Acids and Cupric Acetate, Tetrahedron Lett.* 1998 39:2933-2936; Scheme 1, conditions (a), (b), (e), (f), (i); (ii) by variations of the Ullmann diaryl ether synthesis with Cu(I) salts (J.-F. Marcoux et al., *A General Copper-Catalyzed Synthesis of Diaryl Ethers, J. Am. Chem. Soc.* 1997 119: 10539-540; E. Buck et al, *Ullmann Diaryl Ether Synthesis: Rate Acceleration.by 2,2,6,6-tetramethylheptane-3,5-dione, Org. Lett.* 2002 4(9):1623-1626); conditions (c), (d) and (h); or by nucleophilic aromatic displacement reactions (Sawyer supra pp 5047-5059; conditions Scheme 1(g) and (j). An alternative process utilizing palladium-catalyzed coupling procedures also has been reported (G. Mann et al., *Palladium-Catalyzed Coupling Involving Unactivated Aryl Halides. Sterically Induced Reductive Elimination to Form the C—O Bond in Diaryl Ethers, J. Am. Chem. Soc.,* 1999 121:3224-3225). One skilled in the art will appreciate that optimal procedure will vary depending on the nature and position of substituents on the aryl rings.

SCHEME 8

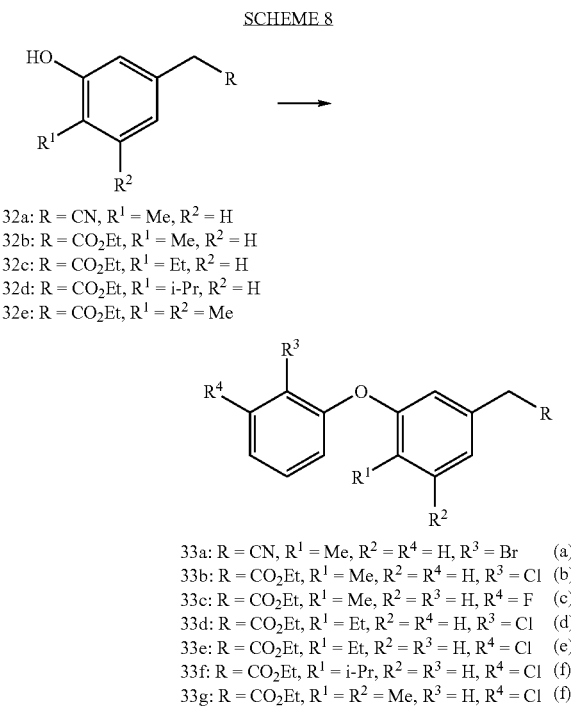

32a: R = CN, R$^1$ = Me, R$^2$ = H
32b: R = CO$_2$Et, R$^1$ = Me, R$^2$ = H
32c: R = CO$_2$Et, R$^1$ = Et, R$^2$ = H
32d: R = CO$_2$Et, R$^1$ = i-Pr, R$^2$ = H
32e: R = CO$_2$Et, R$^1$ = R$^2$ = Me

33a: R = CN, R$^1$ = Me, R$^2$ = R$^4$ = H, R$^3$ = Br (a)
33b: R = CO$_2$Et, R$^1$ = Me, R$^2$ = R$^4$ = H, R$^3$ = Cl (b)
33c: R = CO$_2$Et, R$^1$ = Me, R$^2$ = R$^3$ = H, R$^4$ = F (c)
33d: R = CO$_2$Et, R$^1$ = Et, R$^2$ = R$^4$ = H, R$^3$ = Cl (d)
33e: R = CO$_2$Et, R$^1$ = Et, R$^2$ = R$^3$ = H, R$^4$ = Cl (e)
33f: R = CO$_2$Et, R$^1$ = i-Pr, R$^2$ = R$^3$ = H, R$^4$ = Cl (f)
33g: R = CO$_2$Et, R$^1$ = R$^2$ = Me, R$^3$ = H, R$^4$ = Cl (f)

(a) 2-bromobenzeneboronic acid, Cu(OAc)$_2$, pyridine, 4Å molecular sieves, CH$_2$Cl$_2$;
(b) 2- chlorobenzeneboronic acid, Cu(OAc)$_2$, pyridine, 4Å molecular sieves, CH$_2$Cl$_2$;
(c) m-fluorobromobenzene, CuCl Cs$_2$CO$_3$, TMHD, NMP; (d) 2-iodochlorobenzene; CuCl Cs$_2$CO$_3$, TMHD, NMP; (e) 3-chlorobenzeneboronic acid; Cu(OAc)$_2$, TEA, 4Å molecular sieves, CH$_2$Cl$_2$; (f) 3-chlorobenzeneboronic acid, Cu(OAc)$_2$, TEA, 4Å molecular sieves, CH$_2$Cl$_2$.

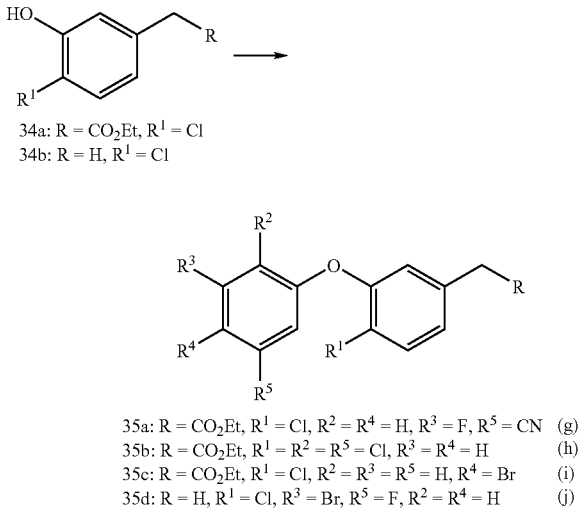

34a: R = CO$_2$Et, R$^1$ = Cl
34b: R = H, R$^1$ = Cl

35a: R = CO$_2$Et, R$^1$ = Cl, R$^2$ = R$^4$ = H, R$^3$ = F, R$^5$ = CN (g)
35b: R = CO$_2$Et, R$^1$ = R$^2$ = R$^5$ = Cl, R$^3$ = R$^4$ = H (h)
35c: R = CO$_2$Et, R$^1$ = Cl, R$^2$ = R$^3$ = R$^5$ = H, R$^4$ = Br (i)
35d: R = H, R$^1$ = Cl, R$^3$ = Br, R$^5$ = F, R$^2$ = R$^4$ = H (j)

(g) 3,5-difluorobenzonitrile, K$_2$CO$_3$, NMP, 120° C.; (h) 2,5-dichlorobromobenzene, CuCl, Cs$_2$CO$_3$, TMHP, NMP 120° C.; (i) 4-bromobenzeneboronic acid, Cu(OAc)$_2$, TEA, 4Å molecular sieves, CH$_2$Cl$_2$; (j) 3,5-dibromofluorobenzene, Cs$_2$CO$_3$, TMHD, NMP.

Substituted m-cresol derivatives are also suitable substrates for coupling using these procedures. After introduction of the meta substituent the intermediate can be converted to the corresponding phenylacetonitrile derivative by bromination and cyanide displacement (Scheme 9).

SCHEME 9

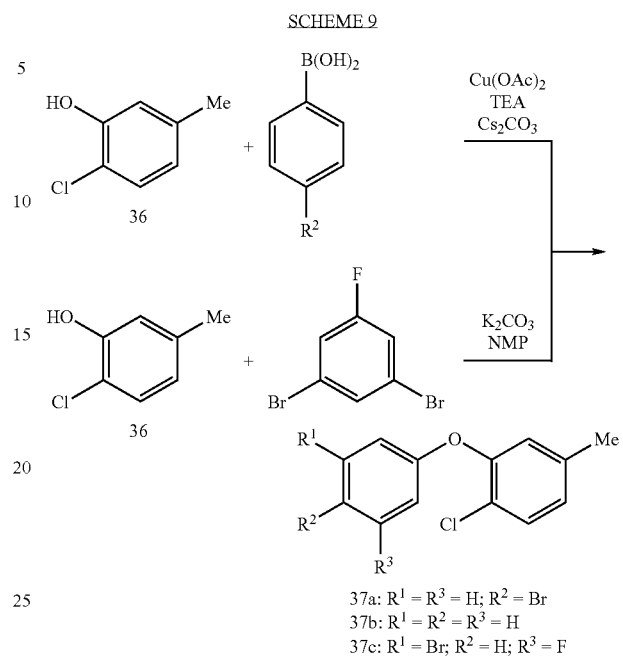

37a: R$^1$ = R$^3$ = H; R$^2$ = Br
37b: R$^1$ = R$^2$ = R$^3$ = H
37c: R$^1$ = Br; R$^2$ = H; R$^3$ = F coupling of compounds with a fuised aryl, heteroaryl or heterocyclic ring to produce diaryl ethers, alkylaryl ethers or arylaralkylethers can be carried out by the same procedures. The preparation of aralkyloxy benzofuranylacetate and aryloxydihydrobenzofuranylacetate derivatives is exemplified in Scheme 10. Aralkoxybenzofurans are prepared by Mitsunobu coupling of the alcohol and the hydroxybenzofuranacetic acid.

SCHEME 10

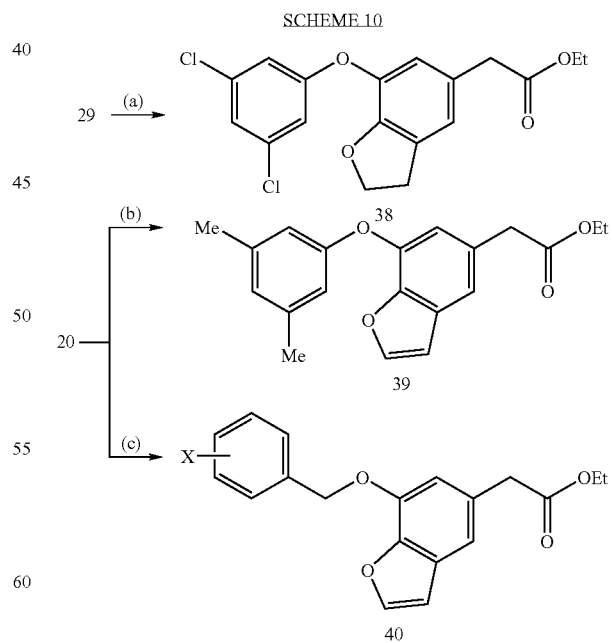

(a) 3,5-dichlorobenzeneboronic acid, Cu(OAc)$_2$, TEA, molecular sieves, CH$_2$Cl$_2$;
(b) 3,5-dimethylbenzeneboronic acid, Cu(OAc)$_2$, TEA, molecular sieves, CH$_2$Cl$_2$;
(c) HOCH$_2$C$_6$C$_4$X, DIAD, PPh$_3$.

Aralkyl aryl ethers were prepared using Mitsunobu conditions (Scheme 11; O. Mitsunobu, *Synthesis* 1981 1-28). Alternatively aralkyl ethers can be prepared via a classical Williamson ether synthesis (J. March, *Advanced Organic Chemistry*; 4th Edition; Wiley & Sons: New York, 1992; pp. 386-87) or utilizing palladium-catalyzed coupling (M. Palucki et al., *Palladium-catalyzed Intermolecular Carbon-Oxygen Bond Formation: A New Synthesis of Aryl Ethers, J. Am. Chem. Soc.* 1997 119:3395-96).

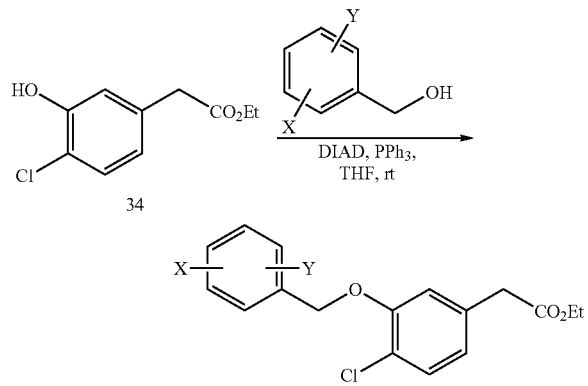

SCHEME 11

Preparation of Diphenylamine Intermediates (Scheme 1; X=NR$^6$)

Diphenylamine compounds with in the scope of the present invention can be prepared by palladium-catalyzed coupling reactions as described by Hartwig (*Transition Metal Catalyzed Synthesis of Aryl Amines and Aryl Ethers from Aryl Halides and Triflates: Scope and Mechanism, Angew. Chem. Int. Ed. Eng.* 1998 37:2046-67)

Preparation of Diphenyl Methane Intermediates (Scheme 1; 2: X=CH$_2$ or C=O)

Diphenylmethane compounds of the present invention can be prepared by reduction of the corresponding benzoyl derivatives 42. While reductions are conveniently carried out with triethylsilylhydride and trifluoroacetic acid, a variety of other procedures to effect this transformation are well known within the art.

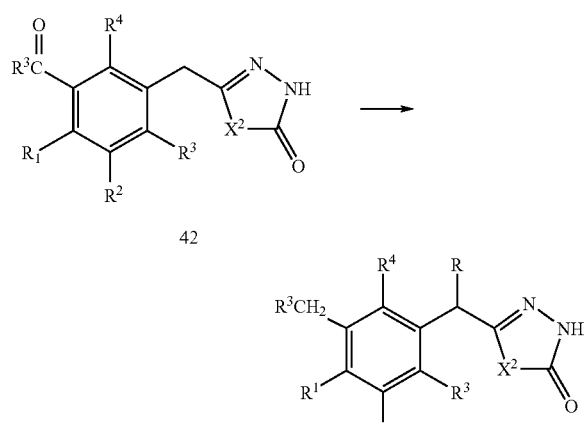

The preparation of the requisite benzoyl derivatives has been described in U.S. Pat. No. 5,886,178 (D. A. Allen et al.). The synthesis of benzoyl substituted benzofuran derivatives have also been reported in U.S. Pat. No. 4,780,480 (J. P. Dunn) and the scientific literature (J. P. Dunn et al. *Analgetic and Antiinflammatory 7-Aroylbenzofuran-5-ylacetic acids and 7-Aroylbenzothiophene-5-ylacetic Acids, J. Med. Chem.* 1986 29:2326) These references are hereby incorporated by reference in its entirety.

Introduction of the Heterocyclic Ring (Scheme 1; 3)

The oxadiazolone, thiadiazolone and triazolone compounds of the present invention can be prepared by cyclization of a diacyl hydrazone derivative according to formula V. Without wishing to be limited by a specific mechanism or sequence of reaction steps, the oxadiazolones can be prepared by treating an acylhydrazone IV with the appropriate acyl derivative and cyclizing the resulting diacyl compound One skilled in the art will appreciate that IV is an ambident nucleophile and initial reaction could be at either the carbonyl oxygen or the nitrogen and subsequent ring closure of either produces the same product

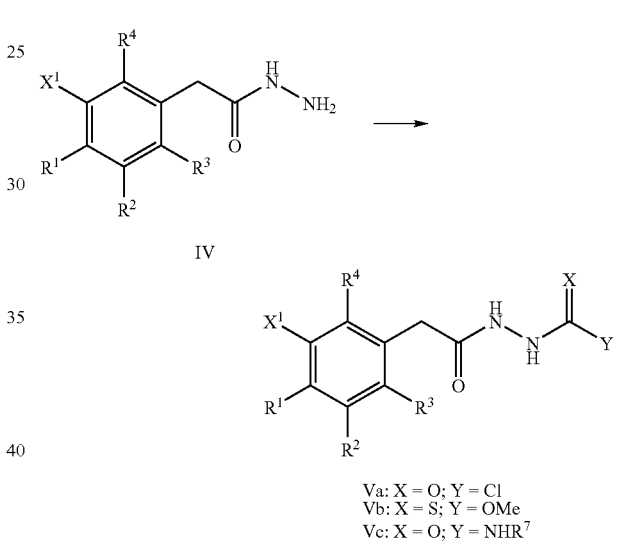

2-Oxo-2,3-dihydro-1,3,4-oxadiazoles 49 can be prepared by cyclization of an acyl hydrazide 46b with phosgene (or equivalents such as carbonyl diimidazole, alkyl chloroformates and the like) to directly produce the desired oxadiazole. (A. Hetzheim, 1,3,4 Oaxadiazoles in *Methoden der Organischen Chemie* (*Houben-Weyl*) E. Schaumann (ed), Hetarene III/Teil 3, Band E8c; Thieme Verlag, Stuttgart; 1994, pp531-536) (Scheme 13) 2-Oxo-2,3-dihydro-1,3,4-thiadiazoles 53 are prepared by condensation of an O-alkyl imidate 51 and methoxythiocarbonyl hydrazide which produce a 2-methoxy-3,4-thidiazole derivative 52 which was hydrolyzed to the corresponding 2-oxo-2,3-dihydro-1,3,4-thiadiazole 53 under acidic conditions (H. Kristinsson et al., *Synthesis of Heterocycles. V 1,3,4-Thiazol-2(3H)one, Helv. Chim. Acta* 1982 65:2606). Alternatively, cyclization of N-acyl-N'-alkoxycarbonyl hydrazides with Lawesson's reagent can directly produce the thiadiazole (B. P. Rasmussen et al. *Bull. Soc. Chim. Fr.* 1985 62). Triazolones 48 were prepared by carbamoylation of an acyl hydrazide 46d with ethyl isocyanate to yield an N-acyl-N-carbamoylhydrazide 47 cyclized to the triazolone 48 upon treatment with methanolic potassium hydroxide.

SCHEME 13

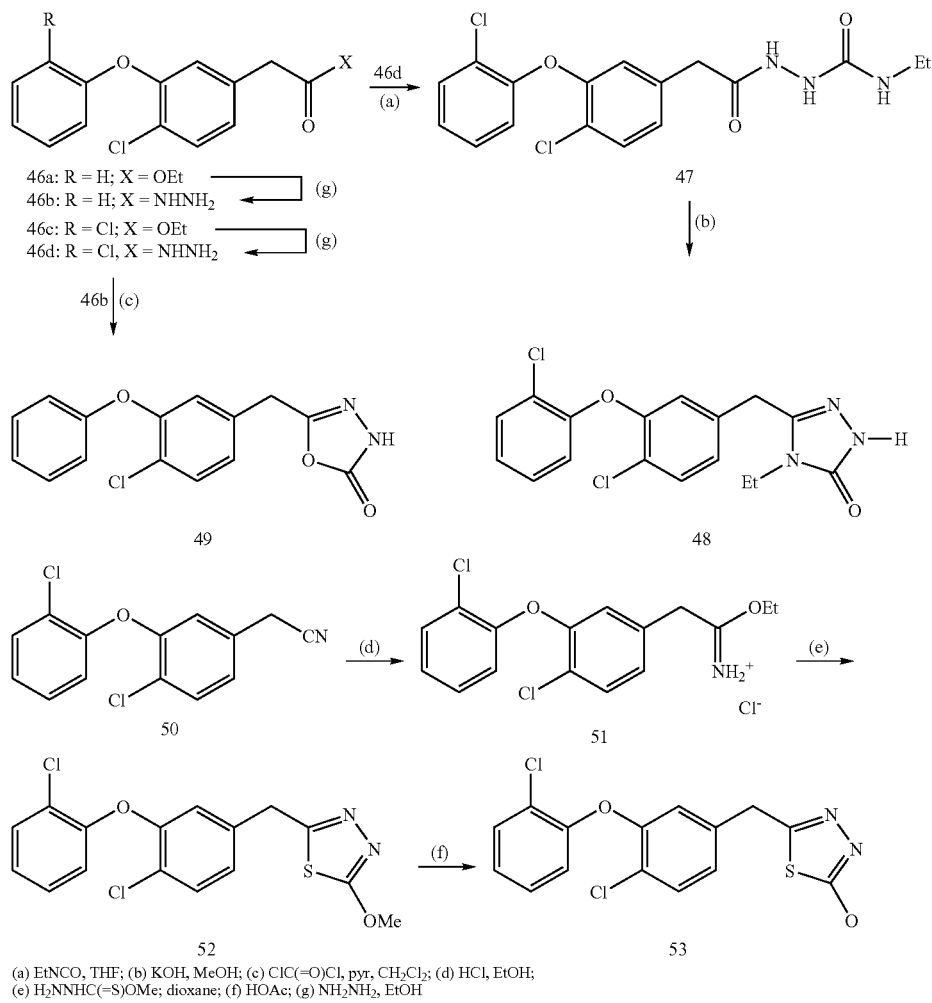

(a) EtNCO, THF; (b) KOH, MeOH; (c) ClC(=O)Cl, pyr, CH₂Cl₂; (d) HCl, EtOH;
(e) H₂NNHC(=S)OMe; dioxane; (f) HOAc; (g) NH₂NH₂, EtOH Dosage and Administration The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use.

The term "excipient" as used herein includes both one and more than one such excipient.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a fmely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the fmely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another nonnucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions, and that the treatment of animals includes the treatment of humans as well as other animals. Furthermore, treatment of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The pharmaceutical compositions in Example 23 are given to enable those skilled in the art to more clearly understand and to practice the present invention. They should not be considered as limiting the scope of the invention, but merely as being illustrative and representative thereof.

The compounds of formula I may be prepared by various methods known in the art of organic chemistry. The starting materials for the syntheses are either readily available from commercial sources or are known or may themselves be prepared by techniques known in the art. The following examples (infra) are given to enable those skilled in the art to more clearly understand and to practice the present invention. They should not be considered as limiting the scope of the invention, but merely as being illustrative and representative thereof. The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. Moreover, the reaction conditions are exemplary and alternative conditions are well known. The reaction sequences in the following examples are not meant to limit the scope of the invention as set forth in the claims.

EXAMPLE 1

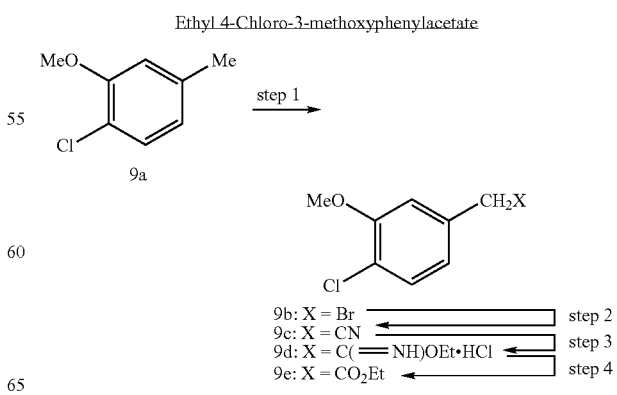

Step 1

A solution of 4-chloro-3-methoxytoluene (9a; 0.5 g; 3.2 mmol), NBS (0.57 g; 3.2 mmol) and benzoyl peroxide (0.031 g; 0.13 mmol) and 32 mL of DCE were heated at reflux for 3 h. The reaction mixture was cooled, diluted with $CH_2Cl_2$ and washed with water and brine. The organic extract was dried filtered and evaporated to yield the bromomethyl compound 9b which was used without further purification.

Step 2

The 28 g (0.166 mmol) of 9b from the previous step, NaCN (28 g; 0.58 mmol; 3.5 equiv.) and 500 mL of 90% aqueous EtOH were stirred at room temperature overnight. The crude residue was partitioned between EtOAc/H2O (359 mL of each), washed with brine, dried, filtered and evaporated. Silica gel chromatography and elution with a gradient (100% hexane→90:10 hexane:EtOAc) yielded 21 g of 9c.

Step 3

Gaseous HCl was slowly bubbled into a cooled solution of 4-chloro-3-methoxyacetonitrile (9b) in toluene (10 mL), ether (10 mL) and EtOH (1 mL) for about 10 min. The reaction was stoppered and stored at −30° C. for one week. TLC failed to detect any remaining starting material. The solvent was evaporated and the yellow solid was stirred with $Et_2O$, filtered and washed with $Et_2O$ and dried in a vacuum oven to yield 0.57 g (90%) of ethyl 4-chloro-3-methoxyphenylmethylirnidate (9d).

Step 4

A solution of 0.57 g of 9d and 10 mL of $H_2O$ was heated at 40° C. for 3 h. The reaction was cooled to rt and extracted with EtOAc. The reaction was dried (MgSO4), filtered and evaporated and the resulting product 9e was used without further purification.

EXAMPLE 2

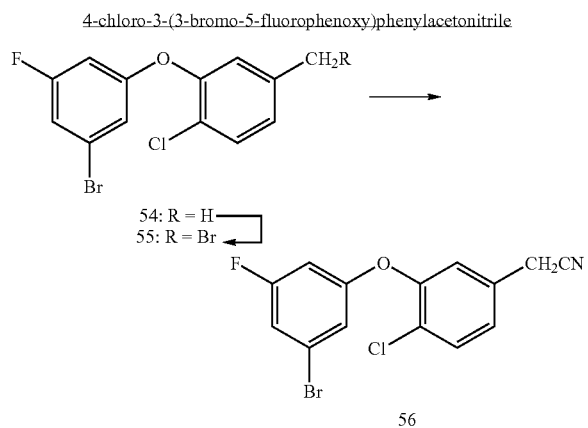

4-chloro-3-(3-bromo-5-fluorophenoxy)phenylacetonitrile

54: R = H
55: R = Br

56

Step 1

A mixture of NBS (1.066 g; 5.99 mmol), benzoyl peroxide (0.069 g; 0.28 mmol) and 54 (1.80 g; 5.70 mmol) and 20 mL of $CCl_4$ were heated to 90° C. for 2.5 h, cooled to rt, poured into water (100 mL) and extracted with $CH_2Cl_2$ (2×80 mL) and the combined organic extracts dried ($Na_2SO_4$), filtered and evaporated to yield 2.25 g of bromomethyl derivative 55 as a colorless oil which was used directly in the subsequent step.

Step 2

A mixture 2.25 g of 55, NaCN (0.839 g; 17.12 mmol) and 20 mL of 90% aqueous ethanol were stirred at room temperature for 24 h. The volume was reduced to about 25% of the original volume in vacuo. The resulting mixture was diluted with EtOAc (80 mL) and poured into 40 mL saturated NaCl and 40 mL of $H_2O$. The organic phase was dried ($Na_2SO_4$), filtered and evaporated and the crude product purified by silica gel chromatography and eluted with an hexane:EtOAc gradient (10:1→6:1) to yield 1.10 g (56.6%) of 56 as a colorless oil.

EXAMPLE 3

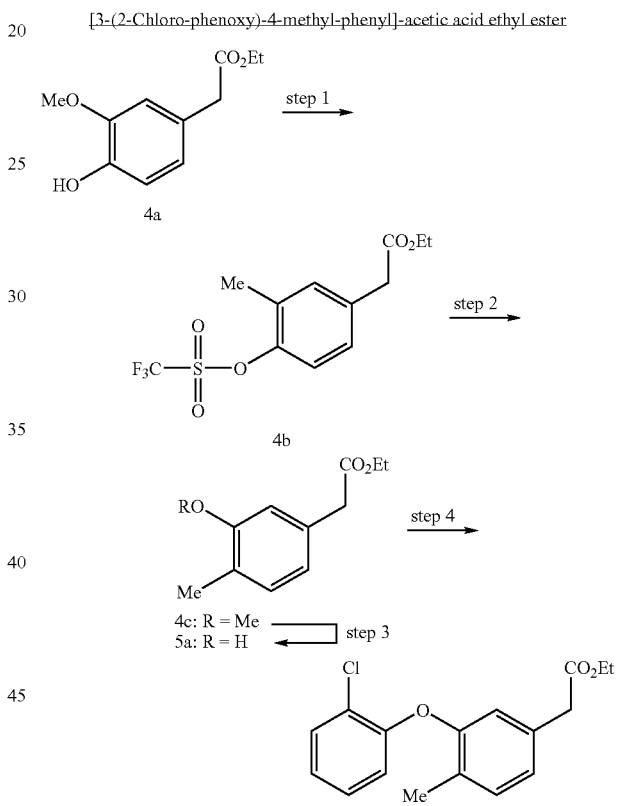

[3-(2-Chloro-phenoxy)-4-methyl-phenyl]-acetic acid ethyl ester

4a

4b

4c: R = Me
5a: R = H

33b

Step 1

To a cooled solution of ethyl 4-hydroxy-3-methoxyphenylacetate (4a; 13.7 g; 65.2 mmol) and 260 mL of $CH_2Cl_2$ under $N_2$ atmosphere was added dropwise triflic anhydride (16 mL; 97.9 mmol) followed by dropwise addition of pyridine (8.9 mL; 8.8 mmol). The reaction was stirred in an ice-water bath for 3 h. The solution was transferred to a separatory funnel and washed with water and brine, dried ($Na_2SO_4$), filtered and evaporated. to yield 21 g (90%) of 4b.

Step 2

To a solution of ethyl 3-methoxy-4-trifluorosulfonyloxyphenylacetate (4b) in 4 mL of THF cooled in an ice-water bath was added slowly a solution of Pd(dppf)Cl$_2$ (0.024 g; 0.029 mmol) and DIBAL-H (6 mL; 0.058 mmol; 1.0 M in PhMe) and a small quantity of THF followed by dimethylzinc (0.29 mL; 0.58 mmol; 2.0 M in PhMe). After addition was completed the ice bath was removed and the reaction allowed to warm to rt and then heated to reflux for 1 h. The reaction was carefully quenched with a small quantity of water, filtered through a pad of CELITE® and the solids washed thoroughly with EtOAc. The combined organic extracts were washed with water and brine, dried (MgSO$_4$) and the solvent evaporated to afford 0.240 g (85%) of ethyl 3-methoxy-4-methylphenylacetate (4c).

Step 3

To a solution of 4c (2.2 g; 8.0 mmol) and 250 mL CH$_2$Cl$_2$ cooled to −78° C. was added dropwise via syringe BBr$_3$ (9.8 mL; 0.104 mol). After 1 h at −78° C. the reaction stirred for 4 h in an ice-water bath. The reaction mixture was recooled to −78° C. and the reaction quenched aqueous NaHCO$_3$ then warmed to rt and the organic phase washed with water, saturated NaHCO$_3$ and brine. The organic phase was dried (MgSO$_4$) and the solvent evaporated to afford 1.4 g of ethyl 3-hydroxy-4-methylphenylacetate (5a).

Step 4

To a suspension of 5a (4.8 g; 25 mmol), 2-chlorobenzeneboronic acid (7.8 g; 50 mmol), Cu(OAc)$_2$ (5 g; 27.5 mmol), powdered 4 Å molecular sieves (15 g) and 250 mL of CH$_2$Cl$_2$. After 4 days starting material was still evident by tlc and an addition 5.0 g of the boronic acid was added. The reaction was stirred for an additional day and the suspension filtered through a pad of CELITE® and silica gel. The solids were washed well with CH$_2$Cl$_2$. The combined filtrates were washed sequentially with 2N HCl (2×25 mL), NaHCO$_3$ (25 mL), water and brine. The extracts were dried (MgSO$_4$), filtered and evaporated. The crude product was purified by silica gel chromatogaphy and eluted with 25% EtOAc:hexane to yield 2.2 g (28%) of 33b Step 6

A mixture of 0.72 g (2.6 mmol) of 57, HOAc (3.5 mL), HCl (7 mL) and H$_2$O (3.5 mL) were heated at reflux for 6 h, cooled to rt, diluted with water and extracted with EtOAc. The combined extracts were washed sequentially with water, sat'd NaHCO$_3$, and brine, dried (Na$_2$SO$_4$), filtered and concentrated. The crude product was purified by chromatography on silica gel. The eluted product, which still contained the 3-chloropyridazine was dissolved in HOAc (20 mL) and NaOAc (0.2 g) and reisolated to yield 0.4 g (50%) of 58 as a white solid; m.p. 116-118.

EXAMPLE 4

3-(2-Chloro-phenoxy)-4-ethyl-phenyl]-acetic acid ethyl ester

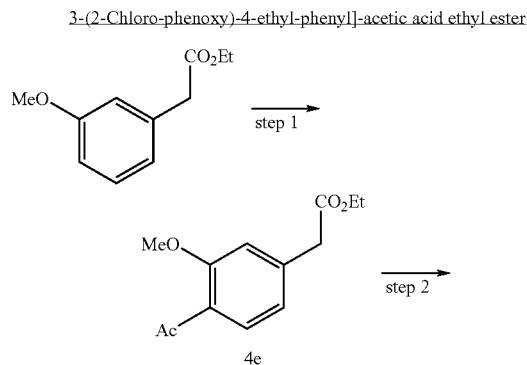

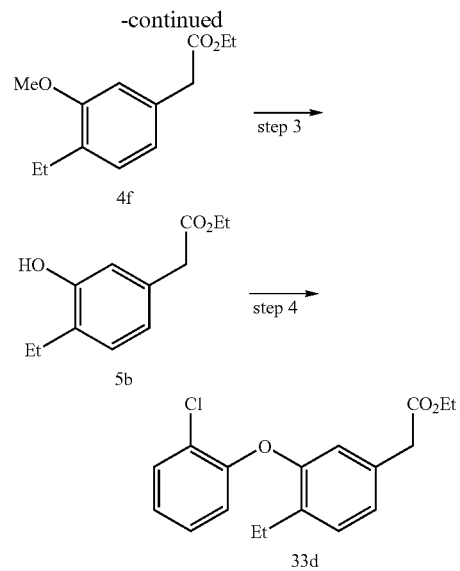

Step 1

To a stirred solution of ethyl 3-methoxyphenylacetate (16.0 g; 82.38 mmol) in CH$_2$Cl$_2$ (200 mL) at rt was added dropwise AcCl (9.88 mL; 138.9 mmol) followed by stannic chloride (16.9 mL; 169 mmol; 1.0 M solution in CH$_2$Cl$_2$) The reaction mixture was stirred at rt for 6 h and poured into an ice-water mixture. The aqueous phase was extracted with CH$_2$Cl$_2$ and the combined extracts were washed with water, dried (Na$_2$SO$_4$) and the solvent removed in vacuo. The crude product 4e was purified by chromatography on silica gel and eluted with CH$_2$Cl$_2$:EtOAc (20:1) to yield 13.96 g (69.5%) of a white solid.

Step 2

To a solution of 4e (19 g; 80.42 mmol) and 200 mL of TFA cooled to 0° C. was added an excess of Et$_3$SiH and the reaction allowed to warm to rt for 3 h. Excess TFA was removed in vacuo and the residue partitioned between water and CH$_2$Cl$_2$. The crude product was purified by chromatography on silica gel and eluted with CH$_2$Cl$_2$:hexane (3:1) to yield 3.0 g (16%) of 4f.

Step 3

A solution of ethyl 4-ethyl-3-methoxyphenylacetate (4f; 3.0 g; 13.50 mmol) and CH$_2$Cl$_2$ (80 mL) was cooled to −78° C. and a solution of (5.10 mL; 53.94 mmol; 1.0 M in CH$_2$Cl$_2$) over 30 min. After 1 h at −78° C. the reaction was allowed to warm to rt and stirred for 12 h. The reaction was cooled in an ice-water bath and the reaction quenched with 20 mL of water. The aqueous phase was extracted with CH$_2$Cl$_2$:EtOAc (4:1 v/v), dried (Na$_2$SO$_4$), filtered and evaporated. The crude product was purified by silica gel chromatography and eluted with a CH$_2$Cl$_2$:EtOAc gradient (100:1→100:4) to yield 5b (2.0 g; 71%): m.s. 209.2 (M+H)$^+$.

Step 4

A solution of ethyl 4-ethyl-3-hydroxyphenylacetate (5b, 0.20 g; 0.96 mmol), 2-iodo-chlorobenzene (0.18 mL; 1.44 mmol), Cs$_2$CO$_3$ (0.469 g; 1.44 mmol), TMHD (0.020 mL; 0.096 mmol) and NMP (15 mL) was degassed with a stream of nitrogen for 15 m. Cuprous chloride (0.48 g; 4.8 mmol) was added and the solution was degassed. The reaction mixture was heated to 120° C. for 11 h then cooled to rt. The suspension was filtered through a pad of CELITE® and the solid washed thoroughly with EtOAc. The combined filtrate was washed with 2N HCl, dried (Na$_2$SO$_4$) and the solvent evaporated. The product was purified by chromatography on silica gel and eluted with EtOAc:hexane (1:10). to yield 0.31 g (39%) of 33d.

EXAMPLE 5

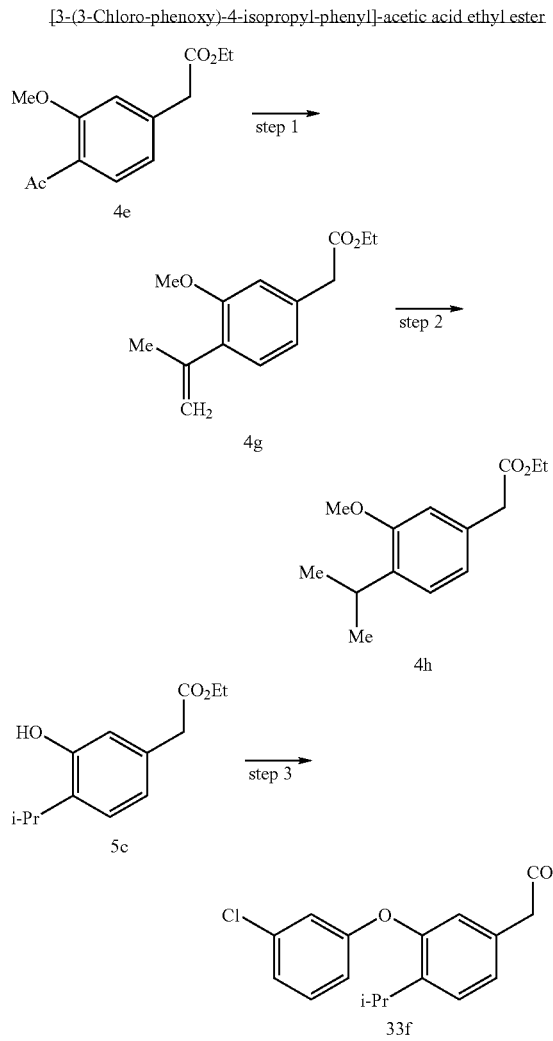

Step 1

To a suspension of PPh$_3$CH$_3^+$Br$^-$ (36.29 g; 101.6 mmol) in THF (150 mL) cooled to −40° C. was added dropwise n-BuLi (40.6 mL; 1.6M in hexanes) and the resulting solution was allowed to warm to −10° C. for 10 m and re-cooled to −40° C. To the resulting solution was added in one portion ethyl 4-acetyl-3-methoxyphenylacetate (see Example 4; step 1) and the reaction mixture was stirred at 0° C. for 30 m and warmed to rt and stirred for an additional 2 h. The reaction mixture was diluted with hexane filtered through a pad of CELITE® and the solids wash with hexane:Et$_2$O (5:1 v/v; 60 mL). The combined organic layers were washed with water (50 mL) and brine (50 mL), dried (Na$_2$SO$_4$), filtered and evaporated to yield a yellow oil. The product was purified by silica gel chromatography and eluted with CH$_2$Cl$_2$:hexane (1:1→2:1) to yield 9.1 g of 4 g.

Step 2

A suspension of 4 g (9.0 g; 38.41 mmol), 5% Pd/C (380 mg) in 50 mL HOAc and 50 mL EtOH was shaken under a hydrogen atmosphere (50 psi) for 7 h. The mixture was filtered through a pad of CELITE® and the filtered catalyst was washed with EtOAc. The solvents were evaporated under reduced pressure and the residue dissolved in MTBE and carefully washed with sat'd HaHCO$_3$, water and brine. The resulting solution was dried (Na$_2$SO$_4$), filtered and evaporated to yield ethyl 4-iso-propyl-3-methoxyphenylacetate (4h; 9.0 g) as a yellow oil.

Step 3

A solution of 4 h (3.38 g; 14.30 mmol) and CH$_2$Cl$_2$ (150 mL) were cooled to −78° C. and a solution of BBr$_3$ (5.41 mL; 57.22 mmol) in 130 mL of CH$_2$Cl$_2$ were added dropwise over a 30 m period. The reaction mixture was stirred at −78° C. for 1 h, allowed to warm to rt for 4 h and re-cooled to −78° C. and carefully quenched with sat'd. NaHCO$_3$ (80 mL). The aqueous layer was extracted with CH$_2$Cl$_2$ (1×100 mL), EtOAc (50 mL) and the combined aqueous layers washed with water and brine, dried (Na$_2$SO$_4$) and evaporated to yield a light brown oil. The phenol was purified by silica gel chromatography and eluted with CH$_2$Cl$_2$:hexane (3:1)→CH$_2$Cl$_2$ →CH$_2$Cl$_2$:EtOAc (100:4) to yield ethyl 4-iso-propy-3-hydroxyphenylacetate (5c; 3.0 g; 94%)

Step 4

To a solution of 5c (1.0 g; 4.5 mmol), 3-chlorobenzeneboronic acid (0.844 g; 5.4 mmol), cupric acetate (0.899 g; 4.95 mmol), 4 Å molecular sieves (5.0 g) and CH$_2$Cl$_2$ (50 mL) was added TEA (3.14 mL; 22.53 mmol) and the reaction was stirred for 3 days. The reaction mixture was filtered through a pad of CELITE®. The top layer containing the molecular sieves was removed and stirred with CH$_2$Cl$_2$ and refiltered. The combined organic filtrates were washed with 2N HCl, brine, dried (Na$_2$SO$_4$), filtered and evaporated. The crude product was chromatographed with silica gel and eluted with a gradient of hexane/EtOAc (90%hexane/EtOAc) to yield 33f (1.0 g; 66%).

Step 6

A mixture of 0.64 g (1.44 mmol) of 59, HOAc (12 mL), HCl (24 mL) and H$_2$O (12 mL) were heated at reflux for 16 h, cooled to rt and extracted with EtOAc. The combined extracts were washed with H$_2$O, dried (Na$_2$SO$_4$), filtered and concentrated in vacuo to afford a brown solid. The crude product was purified by chromatography on silica gel and eluted with a gradient of CH$_2$Cl$_2$:EtOAc (15:1→8:1) to yield 0.10 g (20%) of 60.

EXAMPLE 6

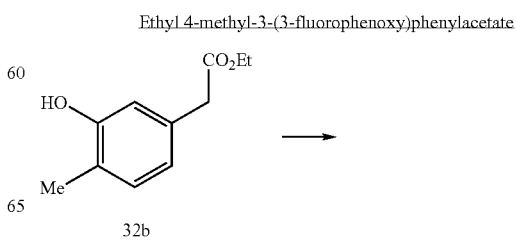

Ethyl 4-methyl-3-(3-fluorophenoxy)phenylacetate

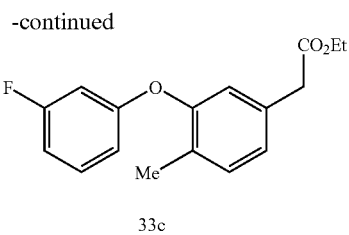

33c

To a stirred solution of 32b (0.80 g; 4.12 mmol) and 7 mL NMP under a $N_2$ atmosphere was added 1-bromo-3-fluorobenzene (0.69 mL; 6.18 mmol), TMHD (0.086 mf; 0.41 mmol), $Cs_2CO_3$ (2.68 g; 8.24 mmol) and Cu(I)Cl (0.204 g; 2.06 mmol). The reaction was heated to 120° C. for 3 h. The reaction mixture was cooled to ambient temperature, and quenched with a mixture of 2 N HCl and EtOAc. The aqueous layer was thrice extracted with EtOAc and the combined organic layers were washed with water and brine, dried ($MgSO_4$), filtered and evaporated to dryness. The crude product was chromatographed on silica gel and eluted with hexane:$Et_2O$ (9:1) which yielded 33c (0.60 g; 50%).

EXAMPLE 7

3-(3-Chloro-phenoxy)-4,5-dimethyl-benzoic acid ethyl ester

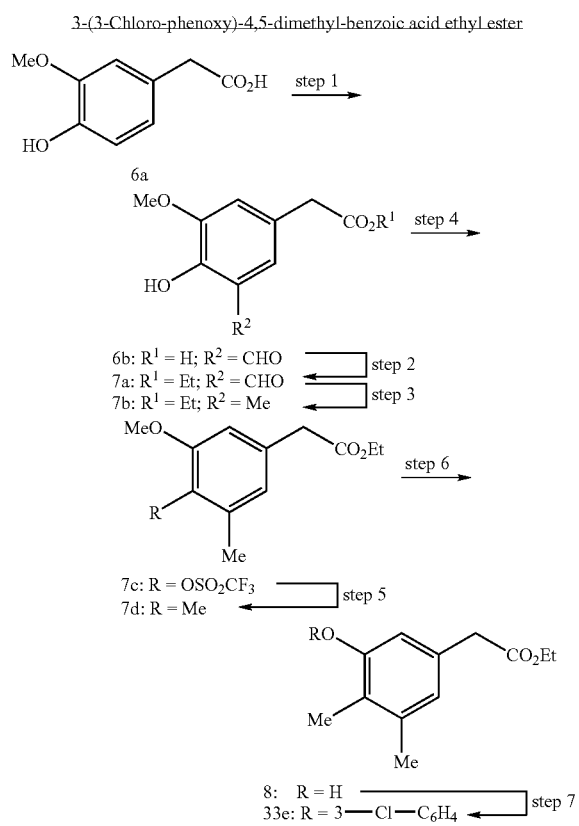

Step 1

A mixture of 4-hydroxy-3-methoxyphenylacetic acid (6a; 1.0 g; 5.49 mmol) and hexamethylenetetranine (0.808 g; 5.76 mmol) and TFA (7 mL) were stirred and heated at 90° C. for 4 h. The reaction was cooled and excess TFA removed in vacuo and 35 mL of ice and water was added to the residue. The resulting dark brown solution was stirred at rt for 20 m. The aqueous solution was extracted with $Et_2O$ (40 mL) and the extract was dried ($Na_2SO_4$), filtered and evaporated to afford 0.70 g of 6b (61%; m.s. $(M+H)^+=211.13$; mw=210).

Step 2

To a solution of 6b (4.0 g; 19.03 mmol) in EtOH (80 mL) was added con $H_2SO_4$ (1 mL). The reaction was heated at reflux for 6 h. Approximately 80% of the EtOH was removed in vacuo and the residue partitioned between EtOAc/$H_2O$ (1:1) the organic phase residue washed with 10% $NaHCO_3$, water (100 mL), dried ($Na_2SO_4$), filtered and evaporated to afford a brown oil 7a (88%; m.s. $(M+H)^+=239.19$; mw=238.3).

Step 3

A mixture of 7a (3.70 g; 15.53 mmol), 5% Pd/C (0.350 g), HOAc (45 mL) were shaken under a H2 atmosphere (40 psi) for 8 h. TLC showed product and the corresponding benzyl alcohol. An additional 300 mg of Pd/C in 25 mL HOAc was added and hydrogenation continued for another 8 h. A second portion of 0.15 g of Pd/C in HOAc (15 mL) was added and reaction continued for another 12 h. The mixture was diluted with EtOAc and filtered through a pad of CELITE®. The catalyst was washed with EtOAc and the combined organic extracts dried ($Na_2SO_4$) and evaporated. The product was purified by silica gel chromatography and eluted with $CH_2Cl_2$:hexane (4:1) to afford 2.64 g of 7b (75.8%).

Step 4

To a solution of 7b (5.87 g; 26.175 mmol) in $CH_2Cl_2$ cooled to 0° C. was added pyridine (3.60 mL; 44.51 mmol) followed by dropwise addition of triflic anhydride (6.605 mL; 39.26 mmol) over about 20 min. The reaction was stirred at 0° C. for 3.5 h. The reaction mixture was extracted with dilute HCl and half-saturated $NaHCO_3$, dried ($Na_2SO_4$) and evaporated to yield 9.41 g of 7c as a brown oil (100%).

Step 5

To a suspension of $PdCl_2$(dppf) (0.650 g; 0785 mmol) in THF (40 mL) cooled to 0° C. was added dropwise a solution of DIBAL-H (1.0 M in PhMe; 1.57 mL; 1.57 mmol). The resulting mixture was stirred at 0° C. for 5 minutes and a solution of 7c in 5 mL of THF was added followed by $Me_2Zn$ (23 mL; 46.0 mmol; 1.0 M in PhMe). The mixture was stirred at 0° C. for 5 m and heated at reflux for 2.5 h then cooled to rt for 30 m. The reaction was poured into dilute HCl and extracted with EtOAc (2×100 mL), dried ($Na_2SO_4$), and evaporated. The crude product was purified by silica gel chromatography and eluted with $CH_2Cl_2$:hexane (1:2→1:1→2:1 v/v) to yield 5.1 g (87.6%) of 8.

Step 6

A solution of ethyl 3,4-dimethyl-5-methoxyphenylacetate (8; 0.560 g; 2.519 mmol) and $CH_2Cl_2$ (40 mL) was cooled to −78° C. and a solution of $BBr_3$ (10.1 mL; 10.1 mmol; 1.0 M in $CH_2Cl_2$) dropwise over 10 min. After 1 h at −78° C. the reaction was allowed to warm to rt and stirred for 12 h. The reaction was cooled in an ice-water bath and the reaction quenched with 15 mL of ice/water. The aqueous phase was extracted with $CH_2Cl_2$:EtOAc (3:1 v/v), dried ($Na_2SO_4$), filtered and evaporated to yield 8 (0.52 g m.s. 209.21 $(M+H)^+$).

Step 7

To a suspension of ethyl 3,4-dimethyl-5-hydroxyphenylacetate (8, 1.0 g; 4.8 mmol), 3-chloro-benzeneboronic acid (0.901 g; 5.762 mmol), Cu(OAc)$_2$ (0.959 g; 5.28 mmol), powdered 4A molecular sieves (5 g) and 40 mL of $CH_2Cl_2$. After 40 h starting material was still evident by tlc and an addition 0.35 g of the boronic acid was added. The reaction was stirred for an additional 72 h. The reaction mixture was filtered through a pad of CELITE® and silica gel. The solids were washed well with $CH_2Cl_2$. The combined filtrates were washed sequentially with 2N HCl (2×25 mL), $NaHCO_3$ (25 mL), water and brine. The extracts were dried ($Na_2SO_4$), filtered and evaporated. The crude product was purified by silica gel chromatogaphy and eluted with EtOAc:hexane (1:15→1:10) to yield 33e (1.0 g; 65%; m.s. $(M+H)^+$=319.34, mw=318).

Step 8

To a solution of 1.0 g of 33e (3.14 mmol), 0.935 g (6.276 mmol) of 3,6-dichloropyrazine in 10 mL dry DMF cooled in an ice-water bath was added portionwise 0.313 g NaH (7.825 mmol; 60% in oil). The reaction stirred at 0° C. for 5 m then was allowed to warm to ambient temperature and stirred for 14 hour. The reaction was poured onto a mixture of ice, water and sodium bisulfate. The mixture was extracted thoroughly with EtOAc and the combined extracts were washed with 5% LiCl, water and brine. The extract was dried ($MgSO_4$), filtered and evaporated and the residue chromatographed on silica gel and eluted with hexane: EtOAc (10:1→8:1) to yield 1.0 g (73.9%) of 61: m.s. $(M+H)^+$=431.29)

Step 9

A mixture of 1.0 g (2.318 mmol) of 61, HOAc (12 mL), HCl (24 mL) and $H_2O$ (12 mL) were heated at reflux for 16 h, cooled to rt and extracted with EtOAc. The combined extracts were washed with $H_2O$, dried ($Na_2SO_4$), filtered and concentrated in vacuo to afford a brown solid. The crude product was purified by chromatography on silica gel and eluted with a gradient of $CH_2Cl_2$:EtOAc (8:1) to yield 0.150 g (18%) of 62 as a brown solid; m.s. $(M+H)^+$=341.27; mw=340.8.

EXAMPLE 8

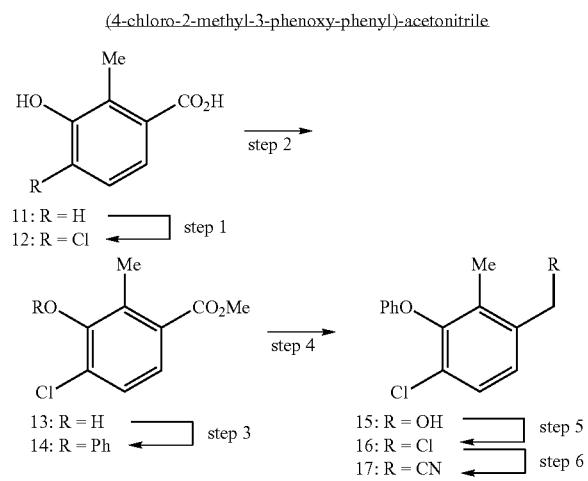

(4-chloro-2-methyl-3-phenoxy-phenyl)-acetonitrile

Step 1

To a suspension of 3-hydroxy-2-methylbenzoic acid (11; 22.8 g; 0.15 mol) and water (300 mL) cooled in an ice-water bath was added 3 M NaOH to adjust pH to about 10 (ca. 60 mL). NaOCl (208 mL; 5.35% aqueous solution; 0.15 mol) was added dropwise over about 30 m while maintaining the temperature between 2-6° C. After the addition was completed, 90 mL of 3 M HCl was added in one portion. The resulting precipitate was collected and dried on a sintered glass filter. The crude product was recrystallized from $Et_2O$: hexane (ca. 3:1) to yield a yellow solid 12 (12.24 g; 44%).

Step 2

A solution of 12 (12.24 g; 65.6 mmol), MEOH (200 mL) and con $H_2SO_4$ (3.85 mL) was stirred overnight at rt then heated to reflux for 6 h. The solution was cooled, concentrated to approximately 10% of the original volume and the residue redissolved in EtOAc. The organic phase was washed with sat'd. $NaHCO_3$ and brine, dried, filtered and evaporated. The crude product was purified by silica gel chromatography and eluted with a EtOAc:hexane gradient (1:9→4:6). The combined fractions were evaporated to yield 13 (8.32 g; 63.2%).

Step 3

To a solution of methyl 4-chloro-3-hydroxy-2-methylbenzoate (13; 1.0 g; 4.98 mmol), benzeneboronic acid (1.52 g; 12.5 mmol), cupric acetate (1.00 g; 5.48 mmol), 4 Å molecular sieves (1 g), and $CH_2Cl_2$ (25 mL) was added TEA (3.47 mL; 24.9 mmol) and the reaction was stirred overnight. Starting material was still detected by tlc and an additional 0.62 g of benzeneboronic acid was added and stirred for another 24 h. The reaction mixture was filtered through a pad of CELITE®. The top layer containing the molecular sieves was washed with $CHCl_3$. The combined organic filtrates were evaporated. The crude product was chromatographed with silica gel and eluted with hexane/ EtOAc gradient (100:0→85:15) to yield 14 (0.82 g; 60%).

Step 4

To a solution of methyl 4-chloro-2-methyl-3-phenoxybenzoate (14; 0.780 g; 2.81 mmol) dissolved in PhMe (20 mL) cooled in an ice-water bath was added dropwise DIBAL-H (7.41 mL; 7.41 mmol; 1.0 M in PhMe) The reaction was quenched by sequentially adding MeOH, $H_2O$, and con HCl. The organic phase was extracted with $Et_2O$. The combined organic extracts were washed with sat'd. $NaHCO_3$, water and brine, dried ($Na_2SO_4$), filter and evaporated to yield 15 as a white oil which was used in the next step without further purification.

Step 5

To a solution of 15 (0.736 g; 2.96 mmol) dissolved in pyridine (10 mL) was added dropwise methanesulfonyl chloride (0.252 µL; 5.92 mmol) over 5 min. After 30 min a small quantity of starting material was evident and an addition 25 µL of methanesulfonyl chloride was added. The reaction was partitioned between Et2O and 5% HCl. The organic phase was twice washed with 5% HCl, water, sat'd. NaHCO3 and brine. The organic extract was dried ($MgSO_4$), filtered and evaporated. The crude product was chromatographed on silica gel eluting with 10% EtOAc:hexane to yield the benzylic chloride 16 (0.220 g) as a colorless oil.

Step 6

The benzyl chloride 16 (0.220 g; 0.82 mmol) was dissolved in EtOH (1 mL) and KCN (0.107 g; 1.64 mmol and 1 mL of water. The mixture was heated to reflux and $CH_3CN$ (0.3 mL) was added to produce a homogenous solution which was allow to reflux overnight. The reaction mixture was concentrated in vacuo and partitioned between water and $CH_2Cl_2$. The organic phase was washed twice with brine, dried ($MgSO_4$), filtered and evaporated to yield 17 (0.210 g) sufficiently pure for further processing.

EXAMPLE 9

Ethyl 4-chloro-3-(3-cyano-5-fluorophenoxy)phenylacetate

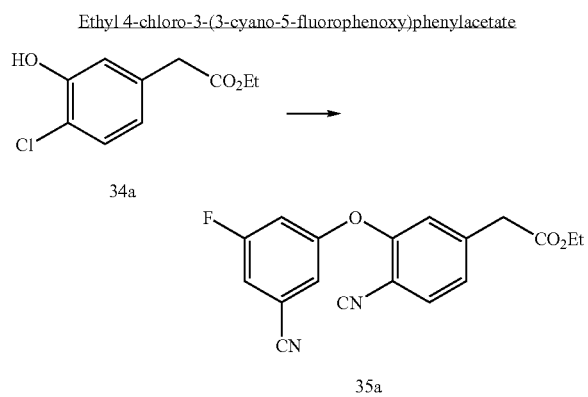

34a

35a

To a solution of ethyl 4-chloro-3-hydroxyphenylacetate (34a; 1.4 g; 6.5 mmol) and NMP (13 mL) was added potassium carbonate (2.7 g; 19.6 mmol) and 1.2 g of 3,5-difluorobenzonitrile (1.2 g; 8.5 mmol). The reaction mixture was heated to 120° C. and monitored by TLC. After 3.5 h an additional 0.9 g of $K_2CO_3$ was added and at 5.5 h an additional 0.9 g of $K_2CO_3$ and 0.3 g of 3,5-difluorobenzonitrile was added. After 8 h of heating the reaction was cooled to rt and the reaction mixture was filtered through a pad of CELITE® and the solid cake was washed well with EtOAc. The filtrate was washed with 2 portions of 2N HCl, 1N NaOH, water and brine. The organic extract was dried ($MgSO_4$), filtered and evaporated to yield 1.3 g of the ether 35a.

EXAMPLE 10

Ethyl 4-chloro-3-(2,5-dichlorophenoxy)phenylacetate

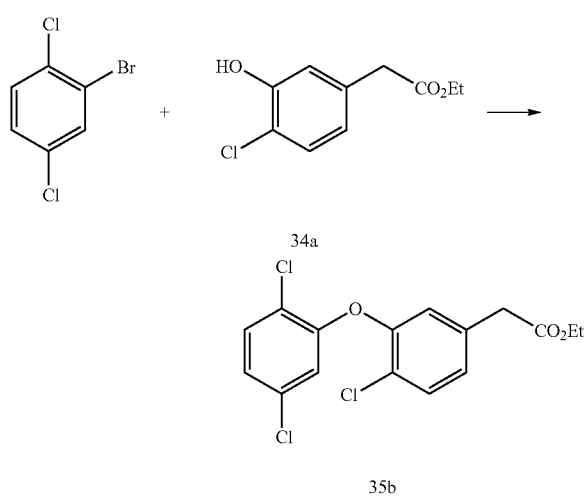

34a

35b

A solution of ethyl 4-chloro-3-hydroxyphenylacetate (34a; 2.0 g; 9.3 mmol), 2,5-dichloro-bromobenzene, $Cs_2CO_3$ (6.0 g; 18.6 mmol), TMHD (0.38 mL; 1.9 mmol) and NMP (15 mL) was degassed with a stream of nitrogen for 15 m. Cuprous chloride (0.5 g; 4.7 mmol) was added and the solution again was degassed. The reaction mixture was heated to 120° C. for 18 h then cooled to rt. The suspension was filtered through a pad of CELITE® and the solid washed thoroughly with EtOAc. The combined filtrate was washed with 2N HCl, dried ($Na_2SO_4$) and the solvent evaporated. The product was purified by chromatography on silica gel and eluted with EtOAc:hexane (1:10) to yield 35b (0.554 g; 16%).

EXAMPLE 11

4-Chloro-3-(4-bromophenoxy)toluene

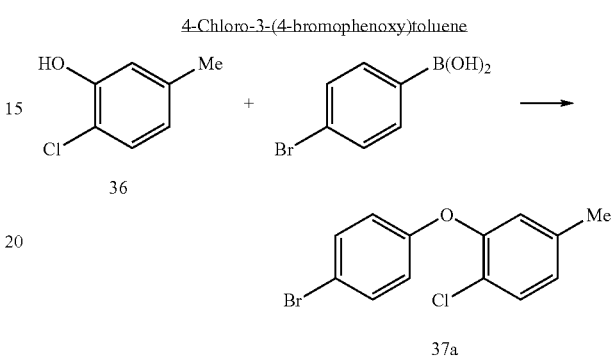

36

37a

A solution of 2-chloro-4-methylphenol (36; 3.0 g; 21 mmol), 4-bromobenzeneboronic acid (5.0 g; 24 mmol), cupric acetate (4.2 g; 23.1 mmol), 4 Å molecular sieves and $CH_2Cl_2$ (210 mL) was added TEA (9.8 mL; 70 mmol) and the reaction was stirred for 3 days. The reaction mixture was filtered through a pad of CELITE®. The top layer containing the molecular sieves was removed and stirred with $CH_2Cl_2$ and refiltered. The combined organic filtrates were washed with 2N HCl, brine, dried ($Na_2SO_4$), filtered and evaporated. The crude product was chromatographed with silica gel and eluted with a gradient of hexane/EtOAc (100:0→90:10) to yield 37a.

EXAMPLE 12

4-chloro-3-phenoxytoluene

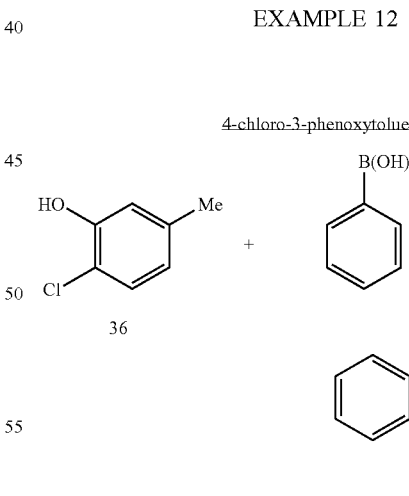

36

37b

To a solution of benzeneboronic acid (1.9 g; 15.8 mmol) dissolved in $CH_2Cl_2$ (250 mL) was added 2-chloro-5-methylphenol (36; 2.5 g; 17.5 mmol), cupric acetate (3.5 g; 19.3 mmol), TEA ((12.3 mL; 87.7 mmol) and 12.5 g of 4 Å molecular sieves. The reaction was stirred for 24 h and an additional aliquot of benzeneboronic (2.4 g; 19.3 mmol) was added and stirring continued for an additional 48 hr. The reaction mixture was filtered through a bed of CELITE® and

EXAMPLE 13

4-Chloro-2-fluoro-3-phenoxytoluene

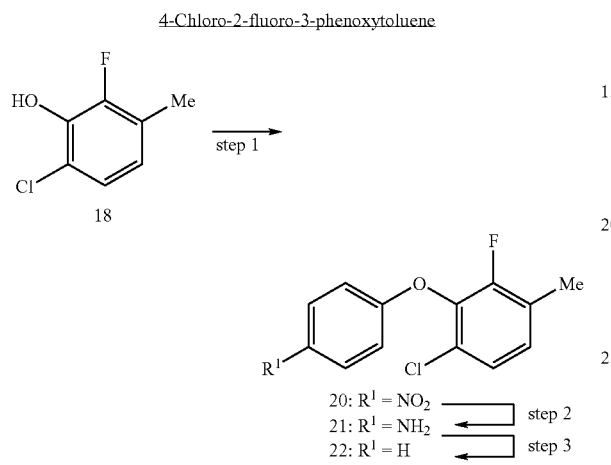

Step 1

A solution of 4-chloro-2-fluoro-3-hydroxytoluene (18; 0.161 g; 1.0 mmol), p-fluoronitro-benzene (0.141 g; 1.0 mmol), $K_2CO_3$ (0.276 g; 2 mmol) and DMF (4 mL) was heated to reflux for 4 h under a $N_2$ atmosphere. The reaction was cooled to rt and poured into water and stirred for several minutes. The aqueous solution was extracted twice with $CH_2Cl_2$ and the combined organic extracts washed with brine, dried ($MgSO_4$), filtered and evaporated to yield 20.

Step 2

A solution of 20 (1.58 g; 5.3 mmol), stannous chloride dihydrate (6.0 g; 26.6 mmol) and EtOH (5 mL) were heated to 70° C. stirred overnight. The reaction mixture was added to a small quantity of ice and made basic with 10% $Na_2CO_3$. The aqueous phase was extracted with EtOAC (5 mL) which resulted in an emulsion. About 7 mL of ethylenediamine was added to chelate tin which resulted in a blue aqueous solution. The EtOAc was washed with water and brine, dried ($NaHCO_3$), filtered and evaporated to yield 1.35 g of 21 which was carried on to the next step.

Step 3

A solution of 21 (0.830 g; 3.3 mmol) was dissolved in HOAc (2.25 mL) and added to a solution of ice-water (7.5 mL) and HCl (1.2 mL). A solution of $NaNO_2$ (0.254 g; 5.6 mmol) and $H_2O$ (1.5 mL) was added over a 10-15 m period. The resulting solution was stirred for several minutes then added dropwise over 15 m to a suspension of $FeSO_4 7H_2O$ (0.917 g; 3.3 mmol) and DMF (10.5 mL). The reaction was stirred for 0.5 h and a mixture of hexanes:EtOAc (1:1; 30 mL) was added. The organic phase was washed thrice with water, dried ($MgSO_4$), filtered and concentrated in vacuo. The dark oil was purified by chromatography on silica gel and eluted with an EtOAc:hexane gradient (0:100→20:80) which yielded 22 as a clear oil (0.450 g; 58%).

EXAMPLE 14

[3-(3-Bromo-5-fluoro-phenoxy)-4-chlorophenyl]acetonitrile (63b)

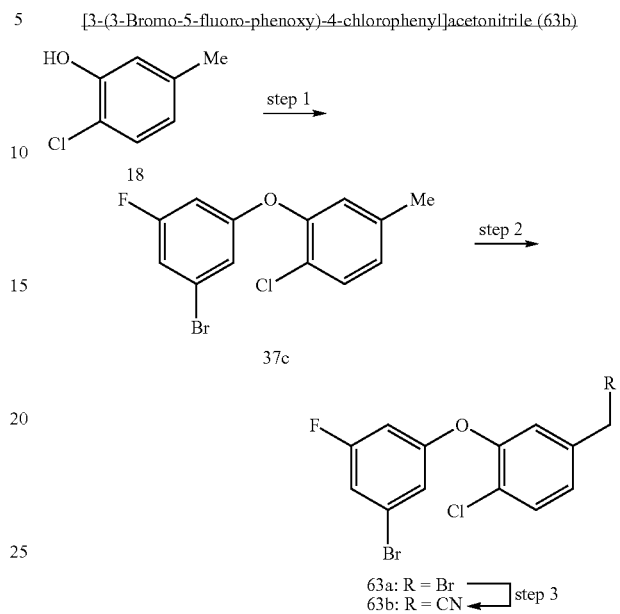

Step 1

Cesium carbonate (11.4 g; 8.79 mmol) was added to a solution of 2-chloro-5-methylphenol (18; 2.5 g; 17.53 mmol) and NMP (16 mL). The resulting slurry was degassed and the flask alternately purged and refilled with nitrogen. 1,3-Dibromo-fluorobenzene (3.54 g; 28.13 mmol), TMHD (0.92 mL; 0.81 g; 4.41 mmol) and Cu(I)Cl (0.87 g; 8.79 mmol) were added sequentially and the reaction mixture was heated to 110° C. for 6 h. The reaction mixture was cooled to ambient temperature, filtered through a bed of CELITE® and the filter cake washed thoroughly with EtOAc. The filtrate was washed sequentially with dilute HCl, dilute NaOH, water and brine. The organic extract was dried ($Na_2SO_4$), filtered and evaporated. The residue was chromatographed on silica gel and eluted with hexane:$Et_2O$ which yielded 1.8 g (32%) of 37c as a colorless oil.

Step 2

A mixture of 37c (1.8 g; 5.704 mmol), NBS (1.066 g; 5.989 mmol), benzoyl peroxide (0.069 g; 0.28 mmol) and $CCl_4$ (20 mL) was heated to 90° C. for 2.5 h. The reaction mixture was cooled to room temperature and poured into 100 mL of $H_2O$. The mixture was extracted with $CH_2Cl_2$ (2×80 mL), dried ($Na_2SO_4$) and evaporated to yield 63a (2.25 g) as a colorless oil.

Step 3

A solution of 63a (2.25 g; 5.704 mmol), NaCN (0.839 g; 17.12 mmol) and 20 mL of 90% aqueous EtOH was stirred at room temperature for 24 h. The solvent was evaporated and the residue partitioned between EtOAc (100 mL) and $H_2O$ (100 mL). The EtOAc phase was washed with $H_2O$ and saturated brine. The organic extracts were dried ($Na_2SO_4$) and evaporated. The crude product was purified by silica gel chromatography and eluted with a hexane/EtOAc gradient (10:1→6:1) to yield 1.10 g (56.6%) of 63b as a colorless oil.

EXAMPLE 15

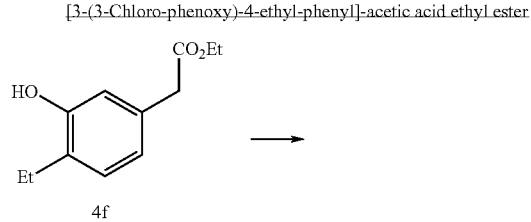

To a solution of ethyl 4-ethyl-3-hydroxyphenylacetate (4f; 1.0 g; 4.81 mmol), 3-chlorobenzeneboronic acid (1.56 g; 10.1 mmol), cupric acetate (0.96 g; 5.29 mmol), 4 Å molecular sieves (5 g), and $CH_2Cl_2$ (48 mL) was added TEA (3.34 mL; 24.05 mmol) and the reaction was stirred for 4 days. The reaction mixture was filtered through a pad of CELITE®. The top layer containing the molecular sieves was removed and stirred with $CH_2Cl_2$ and refiltered. The combined organic filtrates were washed with 2N HCl, brine, dried ($Na_2SO_4$), filtered and evaporated. The crude product was chromatographed with silica gel and eluted with hexane/EtOAc (90%hexane/EtOAc) to yield 33e (0.38 g; 25%).

EXAMPLE 16

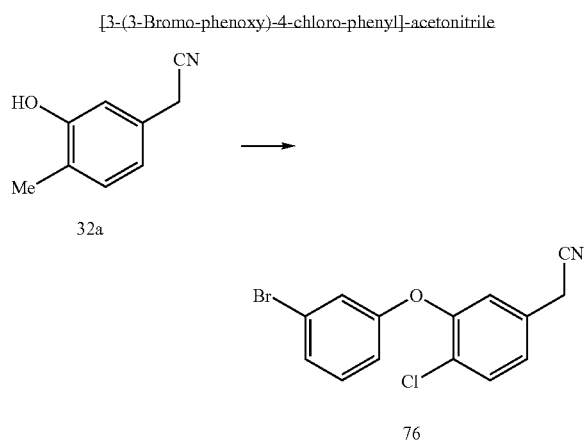

To a flask was charged with 3-hydroxy-4-methylphenylacetonitrile (32a; 0.92 g; 6.2 mmol), Cu(OAc)$_2$ (1.3 g; 6.9 mmol), 3-bromobenzeneboronic acid (1.1 g; 5.5 mmol) and powdered 4 Å molecular sieves, was added $CH_2Cl_2$ (62 mL) followed by pyridine (2.5 mL; 31 mmol). The reaction was stirred at rt for 3 days. The suspension was filtered through a bed of CELITE®/silica gel and the solid washed with $CH_2Cl_2$. The combined filtrates were washed sequentially with 2N HCl (2×25 mL), NaHCO$_3$ (25 mL), water and brine. The extracts were dried (MgSO$_4$), filtered and evaporated. The crude product 76 was sufficiently pure to use in the next step.

EXAMPLE 17

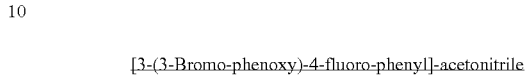

Step 1

To a solution of 2-fluoro4-methylphenol (79; 3.0 g; 24 mmol), 3-bromobenzeneboronic acid (5.3 g; 24 mmol), cupric acetate (4.8 g; 23.1 mmol), 4 Å molecular sieves (15 g) and $CH_2Cl_2$ (240 mL) was added TEA (17 mL; 120 mmol) and the reaction was stirred for 4 days. The molecular sieves were filtered and washed well with $CH_2Cl_2$. The combined organic filtrates were washed with 2N HCl, brine, 2N NaOH, water and brine, dried (Na$_2$SO$_4$), filtered and evaporated. The crude product was chromatographed with silica gel and eluted with hexane:EtOAc (90%hexane:EtOAc) to yield 80 (5.7 g; estimated purity 72%).

Step 2

A solution of 80 (4.1 g; 14.6 mmol), NBS (2.6 g; 14.6 mmol), AIBN (0.25 g; 1.50 mmol) and 146 mL of CCl$_4$ was heated at reflux for 5.0 h, cooled to rt and the precipitated succinimnide filtered through a pad of CELITE®. The filtrate was evaporated and the crude product 81a was sufficiently pure to use in the next step.

The crude bromomethyl compound 81a from the previous step was dissolved in 73 mL of 90% aq. EtOH and 2.5 g of NaCN (49.01 mmol) was added. The reaction mixture was stirred overnight at rt. The solid material was filtered through a pad of CELITE® and the filtrate was evaporated. The crude product purified by silica gel chromatography and eluted with 30% EtOAc:hexane to yield the nitrile 81b (2.4 g; 54%).

EXAMPLE 18

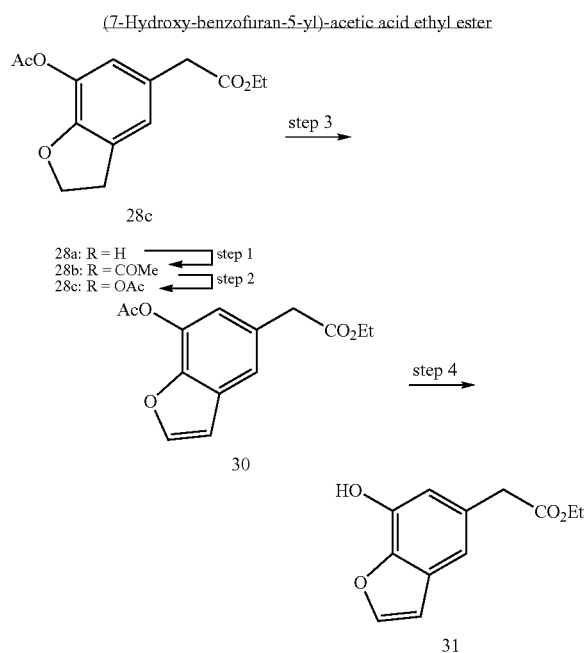

Step 1

To a solution of 28a (5.0 g; 24.2 mmol) and anhydrous $CH_2Cl_2$ (75 mL) was added sequentially acetyl chloride ((2.42 mL; 33.9 mmol) and SnCl4 (5.39 mL; 46.1 mmol; 1 M solution in $CH_2Cl_2$). The reaction was stirred at room temperature for 50 minutes and poured into a mixture of ice and 2 N HCl (200 mL). The organic phase was separated and diluted with about 50 mL of $CH_2Cl_2$ and thrice washed with water (100 mL) and once with brine (100 mL). The organic phase was dried ($MgSO_4$), filtered and evaporated to yield 28b (6.0 g) which contained about 10% of 28a. The crude product was used without further purification.

Step 2

To an ice-cold solution of 28b (6.01 g; 24.2 mmol) and $CH_2Cl_2$ (100 mL) under a nitrogen atmosphere was added sequentially a solution of MCPBA (11.9 g; 48.4 mmol) and $CH_2Cl_2$ (12 mL) followed by TFA (2.14 mL; 27.8 mmol). The reaction mixture was stirred at rt overnight. The reaction mixture was cooled to 0° C. and a 5% aqueous $Na_2SO_3$ solution (150 mL) was added slowly with stirring. The mixture was stirred for 5 minutes after addition was completed and precipitated m-chlorobenzoic acid was filtered. The solid was with $CH_2Cl_2$ and the combined filtrates were washed with 10% NaOH (2×250 mL), 2 N HCl (200 mL), water and brine. The resulting solution was dried ($MgSO_4$), filtered through a pad of CELITE and concentrated in vacuo to yield 28c (4.1 g).

Step 3

To a solution of dihydrofuran derivative 28c (14.6 g; 0.0553 mol) and $CCl_4$ (500 mL) was added NBS (10.3 g; 0.0580 mol) and AIBN (1.4 g). The reaction was heated to reflux for 30 minutes under a nitrogen atmosphere. The reaction was cooled, the solid succinimide filtered, and the organic phase was washed with 0.5 M $NaHSO_4$ (150 mL) and brine. The product was dried (Na2SO4), filtered and evaporated to yield 15.2 g of a yellow syrup. The crude product was purified by silica gel chromatography and eluted with a EtOAc:hexane gradient (3:97→10:90) to yield 10.3 g (78.1%) of 30.

Step 4

A solution of 30 (10.3 g; 39.3 mmol), EtOH (250 mL) and saturated $NaHCO_3$ (100 mL) were heated to reflux for 1 h. The reaction mixture was cooled to room temperature and theEtOH removed in vacuo. Ice was added to the residue aqueous solution and the reaction carefully acidified to about pH 2 with 2 N HCl. The resulting mixture was extracted with EtOAc (2×300 mL) and the combined organic phase washed with brine, dried ($NaSO_4$), filtered and evaporated to yield a brown oil (8.8 g). The crude product was run through a silica gel column with 15% EtOAc:hexane to yield 31 (5.44 g; 62.9%) as a white solid.

EXAMPLE 19

5-(4-Chloro-3-phenoxy-benzyl)-3H-[1,3,4]oxadiazol-2-one (49)

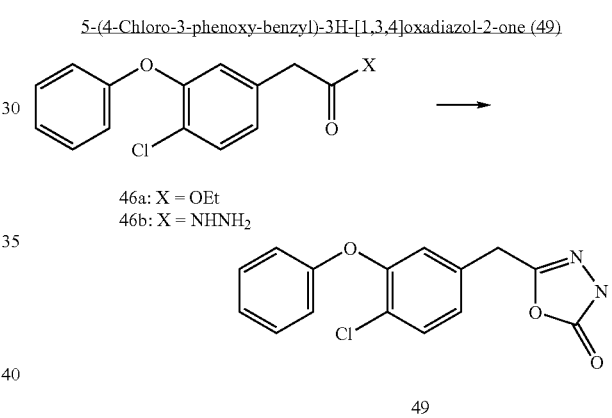

To a solution of ester 46a (517 mg, 2.03 mmol) dissolved in EtOH (10 mL) was added hydrazine hydrate (1.3 mL of an 85% solution) was and the mixture was heated to reflux overnight. The volatile materials were removed, and the residual material was dissolved in EtOAc (50 mL). The solution was washed with brine (20 mL) and dried ($MgSO_4$), filtered, and the volatile materials were evaporated to provide the desired acyl hydrazine 46b (460 mg, 82%) as a white solid. An oven dried 100 mL flask was charged with the 46b (152 mg, 0.55 mmol) and flushed with nitrogen. $CH_2Cl_2$ (6 mL) and pyridine (45 μL, 0.55 mmol) were added, and the solution was stirred for 1 min. A solution of phosgene in methylene chloride (570 μL, 1.93 M, 1.098 mmol) was added dropwise via syringe, and the reaction was stirred for 10 m. Water (15 mL) and $CH_2Cl_2$ (10 mL) were added to the reaction mixture, the layers were separated, and the organic layer was washed with water (10 mL) and brine (10 mL). The solution was dried with anhydrous $Na_2SO_4$, the solution was filtered, and the volatile materials were evaporated to provide 27 (168 mg, 100%; ms (EI): $(M^+)=302$).

EXAMPLE 20

5-[4-Chloro-3-(2-chloro-phenoxy)-benzyl]-3H-[1,3,4]thiadiazol-2-one (31)

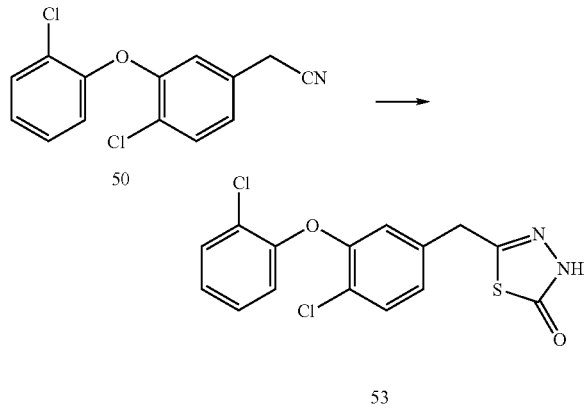

HCl was bubbled through the ice cold solution of nitrile 50 (210 mg, 0.76 mmol) toluene (5 mL) and ethanol (49 µL, 0.87 mmol) for 10 min. The resulting mixture was stored in a sealed flask at 3° C. overnight. Ethyl ether was added to the reaction mixture, and the imidate ester 51 (209 mg) was collected as a white solid by filtration. This material was added in 3 portions to a suspension of hydrazinecarbothioic acid O-methyl ester (55 mg, 0.52 mmol) (Mattes, R. et al. Chem. Ber. 1980 113:1981-88) in anhydrous dioxane (3 mL). The heterogeneous reaction mixture was stirred at rt for 4 h, and then heated to reflux overnight. The reaction was then cooled to rt, and the solvent was removed by evaporation. Chilled water (20 mL) was added, and the mixture was thrice extracted $CH_2Cl_2$ (20 mL). The organic layer was washed with water (20 mL), brine (20 mL), and dried over sodium sulfate. The solution was filtered, and the solvent was evaporated. Purification of the remaining material by flash chromatography (eluent: 25% to 50% ethyl acetate: hexanes) provided the desired methoxythiadiazole 52. A solution of 52, THF (3 mL) and con HCl (1 mL) was stirred overnight. The solution was stirred overnight, ether (20 mL) was added, and the layers were separated. The organic layer was washed with water (10 mL), brine (10 mL), dried ($MgSO_4$). The solvent d was evaporated, and the remaining material was purified by silica gel flash chromatography (10% →25% EtOAc:hexanes) to provide 76 mg of 53 (38% from imidate ester; ms (EI): (M+)=353).

EXAMPLE 21

5-[4-Chloro-3-(2-chloro-phenoxy)-benzyl]-4-methyl-2,4-dihydro-[1,2,4]triazol-3-one (48)

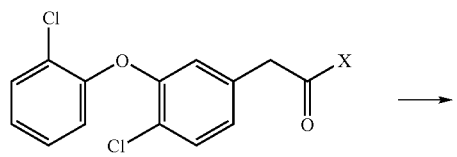

46c: X = OEt
46d: X = $NHNH_2$
47: X = NHNHC(=O)NHEt

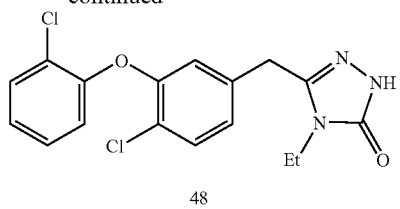

To a solution of ester 46c (219 mg, 0.67 mmol) and EtOH (10 mL) was added hydrazine hydrate (1.2 mL; 85% aqueous solution) and the solution was heated to reflux for 4 h. The volatile materials were removed, and the remaining material was dissolved in EtOAc (50 mL). The solution was washed with water (20 mL), brine (20 mL), and dried ($MgSO_4$). The solution was filtered, and the volatile materials were evaporated to provide acyl hydrazine 46d (200 mg, 96%) as a white solid. To a solution of 46d (96 mg, 0.31 mmol) and anhydrous THF (4 mL) under a $N_2$ atmosphere was added ethyl isocyanate (40 µL, 0.50 mmol) and the mixture was stirred overnight. The volatile materials were evaporated, and the resulting diacylhydrazone 47 dissolved in methanol (4 mL). Potassium hydroxide (173 mg, 3.1 mmol) was added, and the mixture was heated to reflux for 2 days. $CH_2Cl_2$ (20 mL) and water (10 mL) were added, and the aqueous layer was acidified with 10% HCl. The layers were separated, and the aqueous layer was extracted twice with $CH_2Cl_2$ (20 mL). The combined organic layers were washed with water (10 mL), brine (10 mL), and dried ($Na_2SO_4$). The solution was filtered, the volatile materials evaporated, and the residue was purified by silica gel column chromatography and eluted with EtOAc to provide 48 (54 mg, 48% from acylhydrazine 47; ms: 364 (M+H)$^+$).

EXAMPLE 22

HIV Reverse Transcriptase Assay: Inhibitor $IC_{50}$ Determination

HIV-1 RT assay was carried out in 96-well Millipore MultiScreen MADVNOB50 plates using purified recombinant enzyme and a poly(rA)/oligo(dT)$_{16}$ template-primer in a total volume of 50 µL. The assay constituents were 50 mM Tris/HCl, 50 mM NaCl, 1 mM EDTA, 6 mM $MgCl_2$, 5 µM dTTP, 0.15 µCi [$^3$H] dTTP, 5 µg/ml poly (rA) pre annealed to 2.5 µg/ml oligo (dT)$_{16}$ and a range of inhibitor concentrations in a final concentration of 10% DMSO. Reactions were initiated by adding 4 nM HIV-1 RT and after incubation at 37° C. for 30 min, they were stopped by the addition of 50 µl ice cold 20%TCA and allowed to precipitate at 4° C. for 30 min. The precipitates were collected by applying vacuum to the plate and sequentially washing with 3×200 µl of 10% TCA and 2×200 µl 70% ethanol. Finally, the plates were dried and radioactivity counted in a Packard Top-Counter after the addition of 25 µl scintillation fluid per well. $IC_{50}$'s were calculated by plotting % inhibition versus log$_{10}$ inhibitor concentrations.

TABLE 2

| Compound # | RT inhibition $IC_{50}$ (µM) |
| --- | --- |
| 4 | 0.19515 |
| 8 | 0.2865 |

TABLE 2-continued

| Compound # | RT inhibition IC$_{50}$ (μM) |
|---|---|
| 9 | 0.4437 |
| 7 | 0.4473 |

EXAMPLE 23

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (IV)

| Ingredient | % wt./wt. |
|---|---|
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A method for treating an existing HIV infection comprising administering to a host in need thereof a therapeutically effective amount of a compound of formula I

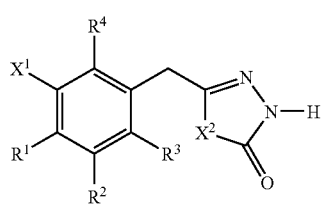

wherein:
- $X^1$ is selected from the group consisting of $R^5O$, $R^5S(O)_n$, $R^5CH_2$, $R^5CH_2O$, $R^5CH_2S(O)_n$, $R^5OCH_2$, $R^5S(O)_n CH_2$ and $NR^5R^6$;
- $X^2$ is selected from the group consisting of O, S, and $NR^7$;
- $R^1$ and $R^2$ are
  - (i) each independently selected from the group consisting of hydrogen, $C_{1-6}$ alkyl, $C_{1-6}$ haloalkyl, $C_{3-8}$ cycloalkyl, $C_{1-6}$ alkylthio, $C_{1-6}$ alkylsulfinyl, $C_{1-6}$ alkylsulfonyl, $C_{1-6}$ haloalkoxy, $C_{1-6}$ haloalkylthio, halogen, amino, alkylamino, dialkylamino, aminoacyl, nitro and cyano; or,
  - (ii) taken together are —CH—CH—CH═CH—, or
  - (iii) taken together along with the carbons to which they are attached to form a five- or six-membered heteroaromatic or heterocyclic ring with a one or two heteroatoms independently selected from the group consisting of O, S and NH;
- $R^3$ and $R^4$ are each independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ haloalkoxy, $C_{1-6}$ haloalkylthio, halogen, amino, alkylamino, dialkylamino, aminoacyl, nitro and cyano;
- $R^5$ is selected from the group consisting of phenyl, naphthyl, pyrdinyl, pyridinyl N-oxide, indolyl, indolyl N-oxide, quinolinyl, quinolinyl N-oxide, pyrimidinyl, pyrazinyl and pyrrolyl; wherein, said phenyl, said naphthyl, said pyrdinyl, said pyridinyl N-oxide said indolyl, said indolyl N-oxide, said quinolinyl, said quinolinyl N-oxide, said pyrimidinyl, said pyrazinyl and said pyrrolyl groups are optionally substituted with one to three substituents independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkoxy, $C_{1-6}$ haloalkylthio, halogen, amino, alkylamino, dialkylamino, aminoacyl, acyl, alkoxycarbonyl, carbamoyl, N-alkylcarbamoyl, N,N-dialkylcarbamoyl, nitro and cyano;
- $R^6$ is hydrogen, $C_{1-6}$ alkyl, or acyl;
- $R^7$ is hydrogen or $C_{1-6}$ alkyl optionally substituted with one or two substituents independently selected from the group consisting of hydroxy, alkoxy, thiol, alkylthio, $C_{1-6}$ alkylsulfinyl, $C_{1-6}$ alkylsulfonyl, halogen, amino, alkylamino, dialkylamino, aminoalkyl, alkylaminoalkyl, and dialkylamino;
- n is an integer from 0 to 2; or acid addition salts thereof.

2. A method according to claim 1 wherein:
- $X^1$ is $OR^5$;
- $R^1$ is methyl, ethyl, trifluoromethyl or halogen;
- $R^2$ and $R^4$ are independently selected from the group consisting of hydrogen, fluoro, chloro, methyl and ethyl;
- $R^3$ is hydrogen or fluoro; and,
- $R^5$ is optionally substituted phenyl.

3. A method for treating HIV infection according to claim 1 further comprising co-administering at least one compound selected from the group consisting of HIV protease inhibitors, nucleoside reverse transcriptase inhibitors, non-nucleoside reverse transcriptase inhibitors, CCR5 inhibitors and viral fusion inhibitors.

4. A method according to claim 3 wherein the reverse transcriptase inhibitor is selected from the group consisting of zidovudine, lamivudine, didanosine, zalcitabine, stavudine, rescriptor, sustiva, viramune, efavirenz, nevirapine and delavirdine and/or the protease inhibitor is selected from the group consisting of saquinavir, ritonavir, nelfinavir, indinavir, amprenavir and lopinavir.

5. A method according to claim 2 for inhibiting a HIV reverse transcriptase.

6. A method according to claim 5 wherein the host is infected with a strain of HIV expressing a reverse transcriptase with at least one mutation compared to wild type virus.

7. A method according to claim 6 wherein said strain of HIV exhibits reduced susceptibility to efavirenz, nevirapine or delavirdine.

* * * * *